United States Patent
Namba et al.

(10) Patent No.: US 6,241,873 B1
(45) Date of Patent: Jun. 5, 2001

(54) SOLD ELECTROLYTES, CARBON DIOXIDE SENSORS AND METHOD FOR CORRECTING THE OUTPUT OF SENSORS

(75) Inventors: Kenryo Namba; Akira Shibue; Shizuko Kumazawa, all of Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 09/118,832

(22) Filed: Jul. 20, 1998

(30) Foreign Application Priority Data

Feb. 20, 1997 (JP) .................................................. 10-055935
Feb. 18, 1998 (JP) .................................................. 10-052966

(51) Int. Cl.$^7$ ................................................ G01N 27/407
(52) U.S. Cl. ......................... 205/784; 204/424; 204/426; 204/421
(58) Field of Search .................... 204/421–429; 429/306, 307, 314; 205/784, 784.5, 785

(56) References Cited

U.S. PATENT DOCUMENTS

| | | | | |
|---|---|---|---|---|
| 3,567,518 | * | 3/1971 | Smythe et al. | 429/307 |
| 5,194,134 | * | 3/1993 | Futata et al. | 204/424 |
| 5,219,679 | * | 6/1993 | Abraham et al. | 429/314 |
| 5,546,802 | * | 8/1996 | Yoshimura et al. | 427/512 |

FOREIGN PATENT DOCUMENTS

| | | | |
|---|---|---|---|
| 2-24465 | * | 5/1990 | (JP) . |
| 4-79542 | | 12/1992 | (JP) . |
| 5-80021 | | 3/1993 | (JP) . |

OTHER PUBLICATIONS

Takehiko Takahashi, et al., Journal of the Electrochemical Society: Solid–State Science And Technology, pp. 1431–1434, "Solid–State Ionics: High–Conductivity Solid Copper Ion Conductors: N–Alkyl (or Hydro)–Hexamethyl-enetetramine Halike–Copper(I) Halike Couble Salts", Oct. 1973.

Takehiko Takahashi, et al., Journal of the Electrochemical Society: Solid–State Science And Technology, pp. 83–86, "Solid State Ionics: High–Conductivity Solid Copper Ion Conductors: N,N'–Dialkyl (or Dihydro)–Triethylenedi-amine Dihalike–Copper(I) Halide Double Salts", Jan. 1975.

Solid Ionics Symposium Lecture Summary Prints, vol. 69, No. 10, pp. 69–70, 1983 month unavailable.

Shigeki Kuwata, et al., Bulletin of Niihama Technical Junior College (Science and Technology Book), vol. 26, No. 98, pp. 67–71, "Solid Electrolyte Carbon Dioxide Sensor Operative at Lower Temperature", 1990, month unavailable (With English Abstract).

(List continued on next page.)

Primary Examiner—T. Tung
(74) Attorney, Agent, or Firm—Oblon, Spivak, McClelland, Maier & Neustadt, P.C.

(57) ABSTRACT

The present invention provides a solid electrolyte having high stability against humidity at room temperature and a carbon dioxide sensor which not only can have sufficient sensitivity but also has excellent responsiveness at room temperature and which is excellent in humidity resistance due to the use of the above solid electrolyte, the solid electrolyte of the present invention being formed by heat-treating a polymer having a quaternary ammonium group in its main chain and having a halide ion as counter ion, and a metal halide, the carbon dioxide sensor of the present invention comprising a detection electrode and a reference electrode formed respectively in contact with a solid electrolyte, the detection electrode containing a metal carbonate which forms a dissociation equilibrium with carbon dioxide, the solid electrolyte being a product formed by heat-treating a compound having an ammonium ion portion and a metal halide or a product formed by heat-treating a polymer having a quaternary ammonium group in its main chain and having a halide ion as counter ion, and a metal halide.

16 Claims, 13 Drawing Sheets

OTHER PUBLICATIONS

Takehiko Takahashi, et al., Journal of the Electrochemical Society: Solid State Science and Technology, pp. 1431–1434, "Solid State Ionics: High–Conductivity Solid Copper Ion Conductors: N–Alkyl (or Hydro)–Hexamethyletetramine Halide–Copper(I) Halide Double Salts", Oct., 1973.

Takehiko Takahashi, et al., Journal of the Electrochemical Society: Solid State Science and Technology, pp. 83–86, "Solid State Ionics: High–Conductivity Solid Ion Conductors: N,N'–Dialkyl (or Dihydro)–Triethylenediamine Dihalide–Copper(I) Halide Double Salts", Jan., 1975.

* cited by examiner

SOLD ELECTROLYTES, CARBON DIOXIDE SENSORS AND METHOD FOR CORRECTING THE OUTPUT OF SENSORS

BACKGROUND OF THE INVENTION

1. Technical Field

The present invention relates to a solid electrolyte, a carbon dioxide sensor for use in indoor or outdoor environmental control, an agricultural process of protected horticulture, prevention against disasters, measurement of an organism surface for a metabolic function, and the like, and a correction method thereof.

2. Technical Background

In recent years, the need for a carbon dioxide sensor is increasing mainly for the detection of contamination of indoor air with widening use of air conditioning, the detection of contamination of air in livestock production facility, the control of plant growth in protected horticulture and various industrial processes, and carbon dioxide sensors according to a variety of methods have been proposed.

Specifically, for example, a carbon dioxide sensor for which an infrared absorption method is applied is practically used. However, the sensor according to the above method has not yet come into wide use since it is large in size and expensive. Further, a semiconductor-applied sensor has been proposed, while the measurement of a carbon dioxide concentration alone is difficult since the sensor has poor selectivity to carbon dioxide.

Meanwhile, several sensors using a solid electrolyte have been proposed as small-sized and inexpensive sensors. Of these sensors, the simplest sensor is a concentration polarization sensor having a pair of electrodes formed on a solid electrolyte such as potassium carbonate, which forms a dissociation equilibrium with carbon dioxide, and the sensor measures an electromotive force based on a concentration difference of ambient gas by bringing a reference gas having a known concentration into contact with one electrode. The problem of the above sensor is that a high temperature of 500 to 700° C. is required for imparting the solid electrolyte with a necessary conductivity and that the solid electrolyte has a property that its material is extremely susceptible to a humidity. The above high temperature can be attained by providing a built-in heater in the sensor. In this case, however, a convection current and a change in temperature are caused in an ambient atmosphere so that an external environment is affected, which is undesirable in some fields of use. There is another problem that the power consumption increases.

In addition to the above concentration polarization sensor, there is a so-called an electromotive force detection sensor obtained by forming a pair of electrodes on a solid electrolyte having an alkali metal ion conductivity such as NASICON (sodium super ion conductor: $Na_3Zr_2Si_2PO_{12}$), forming a layer of metal carbonate such as sodium carbonate which forms a dissociation equilibrium with carbon dioxide on one electrode to be used as a detection electrode, and forming the other electrode as a carbon dioxide non-sensitive electrode. This sensor detects carbon dioxide by utilizing a kind of an electric cell, and the electric cell expression is as follows.

$$CO_2, O_2, Pt|Na_2CO_3||NASICON|Pt, O_2$$

In the interface of the $CO_2$ detection electrode of the above cell, an equilibrium of

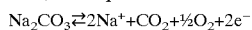

is maintained, and in the interface of the non-sensitive electrode, an equilibrium of

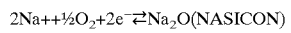

is maintained. Therefore, the total cell reaction is described below.

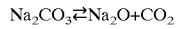

The electromotive force E of the above cell is represented by the expression, $$E = E_0 - (RT/2F)\ln(aNa_2O \cdot PCO_2)$$

wherein $E_0$ is a constant, R is a gas constant, T is an absolute temperature, F is Faraday constant, $2Na_2O$ is an activity of $Na_2O$, and $PCO_2$ is a partial pressure of carbon dioxide gas.

If $2Na_2O$ can be taken as constant, and when or if T can be taken as constant, the partial pressure of carbon dioxide can be determined on the basis of the electromotive force of the above cell. The above explanation is given in the proposal of Maruyama et al in "No. 10 Solid Ionics Symposium Lecture Summary Prints 69 (1983)".

In reality, however, $Na_2O$ cannot be taken as constant in many cases, which causes the partial pressure of carbon dioxide determined on the basis of the electromotive force to vary, as has been pointed out.

Meanwhile, there has been proposed a solid reference electrode type carbon dioxide sensor obtained by attaching, under force, a solid reference electrode which is an electron and oxygen ion conductor to a solid electrolyte formed of an alkali ion conductor (JP-A-7-63726). In this Publication, an Li ion conductor is used as a solid electrolyte, and Li is incorporated into the solid reference electrode so as to keep the activity of $LiO_2$ generated in the interface constant. Since, however, the above sensor also uses an alkali ion conductor, the operation temperature is as high as 400 to 500° C. as shown in Examples in the Publication.

Many electromotive force detection sensors have detection electrodes formed of sodium carbonate, and the humidity resistance thereof is a problem due to their hygroscopicity, while many have been proposed to decrease the influence of humidity. For example, there has been proposed a material which is a solid solution of an alkaline earth metal carbonate and an alkali metal carbonate and does not contain a crystal of the alkali metal carbonate, as a coating material for the detection electrode (JP-A-5-80021, J. Electrochem. Soc., Vol. 130, No. 5, 1384, May 1992).

These electromotive force detection sensors require no reference gas, and reference electrode sides are in an atmosphere to be measured. Measurement values are therefore affected by an oxygen partial pressure. It has been therefore proposed to exclude an influence of a change in an oxygen partial pressure by tightly attaching and laminating an oxide ion conductor on the reference electrode side of an alkali ion conductor (JP-A-7-94013). Further, there are a growing number of examples having a structure in which portions other than the detection electrode are closed with a material impermeable to gases so that the detection electrode alone is in contact with an atmosphere to be measured. As the result of these improvements, stabilized measurement has come to be possible without being much affected by a humidity and an oxygen partial pressure.

For attaining a high conductivity with a solid electrolyte such as NASICON or β-alumina ($NA_2 \, 11AL_2O3$) in an electromotive force detection sensor, however, it is required to provide a built-in heater and secure a high temperature of about 500° C. like the above concentration polarization sensor. Further, an alkali metal carbonate or a solid solution of it with an alkaline earth metal carbonate, used as a detection electrode material, shows not only a low electron conductivity but also a low ion conductivity at room temperature, and a high temperature is therefore required to secure a response speed. A heat of several hundred degrees causes a delicate influence on a measurement environment since it heats vicinities of a sensor even if it is from a small heater, and it causes the convection of air. Further, the power consumption increases, and actuation with an electric cell is therefore difficult.

One report says that the operation of an electromotive force detection sensor at room temperature is attained by using a solid electrolyte prepared by replacing Na ion with Ag ion in NASICON (Bulletin of Niihama Technical Junior College (Science and Technology Book), 26, 98 (1990). Since, however, heating at several hundred degree is required in the case of Na ion, it cannot be thought that the ion conductivity is so improved by only substituting Ag ion. Specifically, the electromotive force at room temperature cannot be said to be sufficient. Further, it is also thought that the responsiveness has a problem.

As a solid electrolyte having a high ion conductivity at room temperature, a Cu ion conductor or an Ag ion conductor is known. Among these are, for example, solid ceramic materials such as $RbAg_4I_5$ ($2.7 \times 10^{-1} Scm^{-1}$, 25° C.), $75AgI.25Ag_2SeO_4$ ($2.2 \times 10^{-2} Scm^{-1}$, 20° C.) and $Ag_3SI$ ($1 \times 10^{-2} Scm^{-1}$, 25° C.), and these can be also used to constitute sensors that can be operated at room temperature.

However, these solid ceramic materials need sintering around 1,000° C., and they are generally poor in humidity resistance. In particular, the Rb-containing material is poor in humidity resistance and fragile. Therefore, the method of producing a sensor is limited.

In recent years, further, for use in Li ion cells, studies have been made on an electrolyte obtained by dissolving lithium perchlorate in a polymer such as polyethylene glycol or a gel type electrolyte formed from a crosslinked polymer and a lithium salt dissolved in a solvent. The later is actively studied in particular, so that a relatively high conductivity at room temperature is achieved. A sensor operable at room temperature can be obtained by combining the above gel electrolyte and electrodes, while the above gel electrolyte has highly hygroscopic properties. Differing from a cell having an electrolyte closed, the sensor has an electrolyte exposed to ambient atmosphere, and both the metal salt and the polymer are therefore liable to absorb water, to cause a change in electric conductivity, so that a stable electromotive force can be no longer attained.

SUMMARY OF THE INVENTION

The present invention has been made under the circumstances. It is an object of the present invention to provide a solid electrolyte having high stability against humidity and a carbon dioxide sensor which uses the solid electrolyte, which attains a sufficient sensitivity at room temperature and is excellent in responsiveness and which is excellent in humidity resistance. In addition thereto, further, it is another object of the present invention to provide a carbon dioxide sensor which exhibits a high electromotive force change as well depending upon a change in the concentration of carbon dioxide.

Further, in an electromotive force detection carbon dioxide sensor, the influence of water thereon is almost removed, e.g., by employing a structure in which portions other than the detection electrode are tightly closed with a material impermeable to gases since the absolute humidity is low at a high temperature (350° C. or higher). In room temperature, however, the absolute humidity is high, the electromotive force varies due to a relative humidity (humidity), and it is therefore difficult to attain stable performances. Further, since the electromotive force is according to the expression of Nernst, $$E=E_0-(RT/2F)\ln(aAg_2O.PCO_2)$$

the electromotive force has a linear relationship with the temperature of the device. Unlike a sensor having a built-in heater for measurement at a constant temperature, the electromotive force detection sensor shows a change in electromotive force depending upon ambient temperatures, which results in an error. For attaining stable performances with an electromotive force detection carbon dioxide sensor operable at room temperature, it is required to remove the influences of humidity and temperature on the electromotive force.

It is another object of the present invention to provide a highly accurate carbon dioxide sensor which can have a sufficient sensitivity at room temperature and is almost free from the influences of humidity and temperature, and an output correction method thereof.

The above objects are achieved by the present invention below.

(1) A solid electrolyte formed by heat-treating a polymer having a quaternary ammonium group in its main chain and having a halide ion as counter ion, and a metal halide.

(2) A solid electrolyte according to the above (1), wherein the polymer is a polymer from a diamine compound and a dihalogen compound.

(3) A solid electrolyte according to the above (1), wherein the metal halide is a halide of Ag or Cu.

(4) A carbon dioxide sensor comprising a detection electrode and a reference electrode formed respectively in contact with a solid electrolyte, the detection electrode containing a metal carbonate which forms a dissociation equilibrium with carbon dioxide, the solid electrolyte being a product formed by heat-treating a compound having an ammonium ion portion and a metal halide.

(5) A carbon dioxide sensor according to the above (4), wherein the compound having an ammonium ion portion is an alkylammonium halide, an arylammonium halide or a nitrogen-containing cyclic ammonium halide.

(6) A carbon dioxide sensor according to the above (4), wherein the solid electrolyte is a product formed by heat-treating a polymer having a quaternary ammonium group in its main chain and having a halide ion as counter ion, and a metal halide.

(7) A carbon dioxide sensor according to the above (6), wherein the polymer is a polymer from a diamine compound and a dihalogen compound.

(8) A carbon dioxide sensor according to the above (4), wherein the metal halide is a halide of Ag or Cu.

(9) A carbon dioxide sensor according to the above (4), wherein the detection electrode contains at least 2 metal carbonates which form dissociation equilibrium with carbon dioxide.

(10) A carbon dioxide sensor according to the above (9), wherein the metal carbonates are silver carbonate and alkali metal carbonate.

(11) A carbon dioxide sensor according to the above (9), wherein the metal carbonates are copper carbonate and alkali metal carbonate.

(12) A carbon dioxide sensor according to the above (10), wherein the alkali metal carbonate is contained in an amount of 50% by weight or less.

(13) A carbon dioxide sensor according to the above (12), wherein the alkali metal carbonate is contained in an amount of 5 to 10% by weight.

(14) A carbon dioxide sensor device having the carbon dioxide sensor recited in the above (4) and further having a temperature detection element for detecting a temperature of the carbon dioxide sensor and/or a humidity detection element for detecting a humidity around the carbon dioxide sensor.

(15) An output correction method which comprises providing the carbon dioxide sensor device recited in the above (4), measuring an electromotive force with the carbon dioxide sensor and at the same time detecting a temperature with the temperature detection element, correcting the electromotive force with a linear relational expression of the electromotive force and the temperature, and determining a carbon dioxide concentration on the basis of the corrected electromotive force.

(16) An output correction method which comprises providing the carbon dioxide sensor device recited in the above (4), measuring an electromotive force with the carbon dioxide sensor and at the same time detecting a humidity with the humidity detection element, correcting the electromotive force with a linear relational expression of the electromotive force and the humidity, and determining a carbon dioxide concentration on the basis of the corrected electromotive force.

(17) An output correction method which comprises providing the carbon dioxide sensor device recited in the above (4), measuring an electromotive force with the carbon dioxide sensor and at the same time detecting a temperature with the temperature detection element and detecting a humidity with the humidity detection element, correcting the electromotive force with a linear relational expression of the electromotive force and the temperature and a linear relational expression of the electromotive force and the humidity, and determining a carbon dioxide concentration on the basis of the corrected electromotive force.

FUNCTION

The present invention uses the above solid electrolyte, and therefore it attains a sufficient ion conductivity at room temperature and is also excellent in responsiveness. Further, since the above solid electrolyte is excellent in humidity resistance, the influence of an ambient humidity on measurement is small. When the above polymer is used as a material for the solid electrolyte, particularly, the humidity resistance improves and the solid electrolyte is improved in mechanical strength. The above polymer itself has high hygroscopicity, while the hygroscopicity remarkably decreases by converting it to an organic-inorganic composite solid electrolyte by reacting it with a metal halide such as silver halide. The hydroscopicity further decreases when a dihalogen compound in particular is used.

Further, when at least two metal carbonates are used in the detection electrode, the change in the electromotive force increases depending upon a change in the concentration of carbon dioxide to be measured at room temperature, and the responsiveness improves. Further, when one of the two metal carbonates is an alkali metal carbonate, particularly, lithium carbonate, a stable difference in the electromotive force can be obtained.

JP-B-2-24465 discloses a humidity sensor using, as a humidity-sensitive polymer, a polymer having a quaternary ammonium group in its main chain (so-called ionene polymer), i.e., a polymer which is used in the present invention as a raw material for the solid electrolyte. Further, U.S. Pat. No. 5,546,802 also discloses a humidity sensor. The latter humidity sensor includes a humidity-sensitive thin film formed of a polymer compound prepared by introducing an ethylenically unsaturated reactive group into the polymer of the former and crosslinking the same. However, these humidity sensors utilize a change in ion conductivity based on the humidity absorption of a humidity-sensitive thin film, and are completely different from the present invention which requires the prevention of a humidity-induced change in the ion conductivity of the solid electrolyte. Naturally, the above Publications do not describe to the effect that the above polymer or the above polymer compound and a metal halide are allowed to react with each other by heat treatment.

Further, J. Electrochem. Soc.: SOLID STATE SCIENCE, 1536–1539, December 1970 and the said Journal, 1144–1147, July 1971 describe a solid electrolyte formed of double salts of substituted ammonium iodide and silver iodide. Further, J. Electrochem. Soc.: ELECTROCHEMICAL SCIENCE AND TECHNOLOGY, 1291–1296, October 1975, J. Electrochem. Soc.: SOLID STATE SCIENCE, 1431–1434, October 1973, and the said Journal 83–86, January 1975 describe high-conductivity solid electrolytes formed of double salts of substituted organic ammonium halide and copper halide. These solid electrolytes are the same as part of the solid electrolyte used in the present invention, while these literatures do not describe to the effect that the solid electrolyte is applied to a carbon dioxide sensor.

Further, JP-A-2-232557 proposes a carbon dioxide sensor having a detection electrode formed of a substance containing a mixture of at least two metal carbonates. Since, however, the solid electrolyte used therein is β-alumina, it is required to have a built-in heater and heat at 500° C. or higher for measurement. It describes nothing concerning the measurement at room temperature like the measurement in the present invention. Further, the metal carbonates used are sodium carbonate and other alkali metal carbonate.

The above carbon dioxide sensor of the present invention operates at room temperature, is excellent in responsiveness, is superior to any conventional one in humidity resistance and is almost free of the absorption of water into the solid electrolyte. However, the proton ion conductivity may increase or the electromotive force may change when water is adsorbed on the solid electrolyte surface or when a very small amount of water infiltrates the vicinity of the solid electrolyte surface.

It is therefore preferred to provide a structure having a temperature detection element for detecting a temperature of the carbon dioxide sensor and a humidity detection element for detecting a humidity around the carbon dioxide sensor in addition to the above carbon dioxide sensor. In this carbon dioxide sensor device, an electromotive force is measured with the carbon dioxide sensor, and at the same time, a temperature is detected with the temperature detection element, a humidity is detected with the humidity detection element, the electromotive force is corrected with regard to the temperature and the humidity, and a carbon dioxide concentration is determined on the basis of the corrected electromotive force. The electromotive force and the temperature have, and the electromotive force and the humidity have, a linear relationship. The electromotive force is corrected with regard to the temperature and the humidity on the basis of the above linear expressions, whereby a carbon dioxide to be measured can be accurately measured for a concentration, particularly, at room temperature.

A number of carbon dioxide sensors requiring no correction with regard to a humidity have been devised so far, while the device temperature is set at 300° C. or higher in all of these. Since a molar percentage of water to be thermodynamically determined at 300° C. or higher is very small as compared with the counterpart at room temperature (25° C.), the influence of water during the measurement is negligible. As described above, however, a heater-applied sensor cannot overcome the problem that since the device is heated with a heater, the measurement environment changes due to a convection or a heat conduction or the power consumption increases, or the problem that it takes a long time to obtain a stable electromotive force by removing water which infiltrates during a non-heating period.

DESCRIPTION OF PREFERRED EMBODIMENTS

Figure 1:
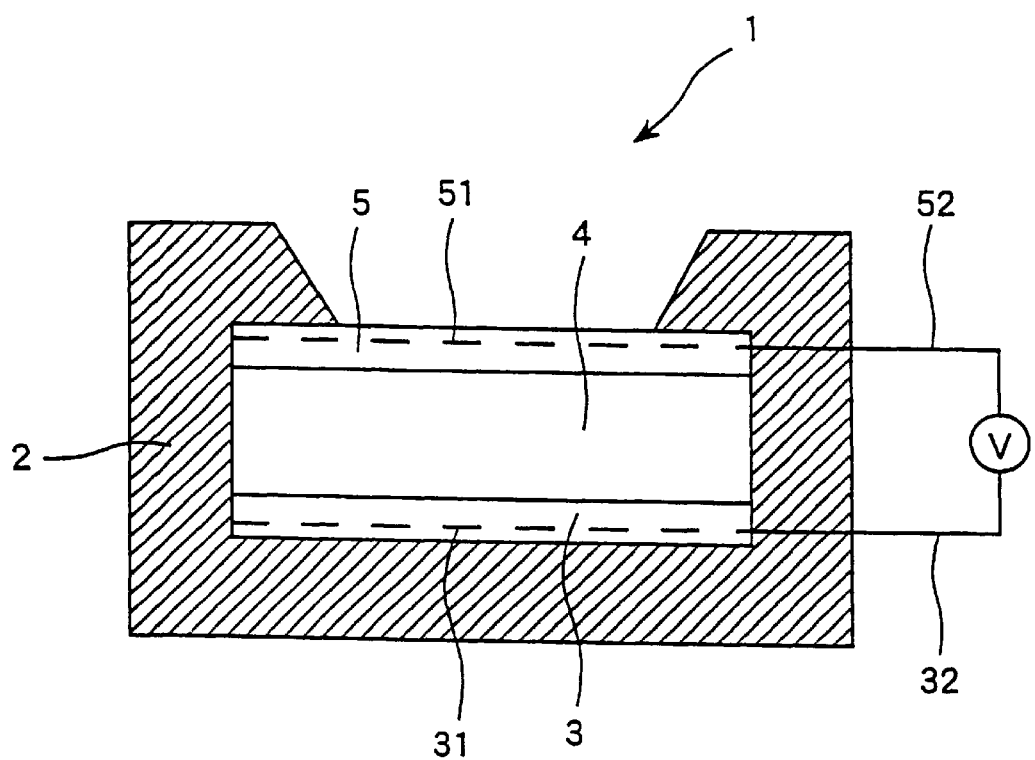
FIG. 1 is a cross-sectional view showing a configuration of a carbon dioxide sensor of the present invention.

The carbon dioxide sensor of the present invention has a detection electrode and a reference electrode formed respectively in contact with a solid electrolyte.

The present invention uses, as a solid electrolyte, a product formed by heat-treating a compound having an ammonium ion portion and a metal halide.

A material for Solid Electrolyte (polymer)

As the above compound having an ammonium ion portion, it is preferred to use a polymer having a quaternary ammonium group in its main chain and having a halide ion as counter ion.

The above polymer is preferably a polymer of the following formula (1).

Formula (1)

In the polymer of the formula (1), the content of a quaternary ammonium salt group as a cation equivalent per mass of the polymer unit is 1.2 to 30 meq/g, preferably 1.5 to 25 meq/g.

In the formula (1), each of A and B is a divalent group.

The divalent group represented by A is preferably an alkylene group, an alkenylene group, an arylene group or a combination of these, and hydroxy, an alkyl group such as methyl or a carbamoyl group may be substituted thereon.

The total number of carbon atoms of the alkylene group is preferably 1 to 20. When hydroxy is substituted, the number of the substituent(s) is preferably 1 to 5.

The total number of carbon atoms of the alkenylene group is preferably 2 to 10.

The total number of carbon atoms of the arylene group is preferably 6 to 20.

When the divalent group is a combination of these, the total number of carbon atoms of the combination is preferably 3 to 20.

Specifically, the divalent group preferably includes —$(CH_2)_m$— (m=an integer of 1 to 20), —$CH_2CH$=$CH$—$CH_2$—, —$CH_2$—$CH(OH)$—$CH_2$—, —$CH(CH_3)$—$CH_2$—$CH_2$—, —$C_6H_4$—$C_6H_4$— and —$C_6H_4$—$CH(OH)$—$C_6H_4$—.

The divalent group represented by B is preferably an alkylene group, an alkylene group having at least one of an oxy group (—O—) and a carbonyl group (—CO—) interposed, an alkenylene group or a combination of these. A hydroxy group or an alkenyl group such as a vinyl group may be substituted thereon.

The total number of carbon atoms of the alkylene group is preferably 1 to 20. When hydroxy is substituted, the number of the substituent(s) is preferably 1 to 5. Further, when —O— or —CO— is interposed, the total number of the interposed group(s) is preferably 1 to 5.

The total number of carbon atoms of the alkenylene group is preferably 2 to 10. The total number of carbon atoms of the arylene group is preferably 6 to 20. When the divalent group is a combination of these, the total number of carbon atoms of the combination is preferably 3 to 20.

Specifically, the divalent group preferably includes —$(CH_2)_m$— (m=an integer of 1 to 20), —$(CH_2)_2$—$CH(OH)$—$CH_2$—, —$CH_2$—$CH(OH)$—$CH_2$—, —$CH_2$—$CH$=$CH$—$CH_2$—, —$CH_2$—$CH(CH$=$CH_2)$—, —$(CH_2$—$CH_2$—$O)_2$—$(CH_2)_2$—, —$CH_2$—$(CO)$—$CH_2$— and —$CH_2$—$C_6H_4$—$CH_2$—.

Each of $R_1$, $R_2$, $R_3$ and $R_4$ is an alkyl group or an alkenyl group.

The alkyl group represented by each of $R_1$ to $R_4$ preferably has 1 to 10 carbon atoms. The alkyl group may have a substituent, while an alkyl group having no substituent is preferred. Specifically, the alkyl group is preferably methyl, ethyl, propyl or butyl.

The alkenyl group represented by each of $R_1$ to $R_4$ preferably has 1 to 10 carbon atoms. The alkenyl group may have a substituent, while an alkenyl group having no substituent is preferred. Specifically, the alkenyl group is preferably vinyl, allyl, propenyl or butenyl.

$R_1$ and $R_2$, $R_1$ and A or part of A, $R_2$ and A or part of A, $R_3$ and $R_4$, $R_3$ and A or part of A, $R_4$ and A or part of A, $R_2$ and $R_3$ or $R_4$, or $R_2$ and $R_3$ or $R_4$ may bond to each other and form a ring together with a nitrogen atom (N). The above ring is preferably a five-membered or six-membered, particularly preferably a six-membered, nitrogen-containing heterocyclic ring, and further, it may be a crosslinked ring. The above nitrogen-containing heterocyclic ring includes a pyridine ring, a 1,4-diazabicyclo[2.2.2]octane ring, piperidine ring, a piperazine ring and a pyrazine ring. Of these, 1,4-diazabicyclo[2.2.2]octane ring is preferred. A carbamoyl group or the like may be substituted thereon in some cases.

In the formula (1), X is a halogen atom. Specifically, it may be a chlorine atom, a bromine atom or an iodine atom, and an iodine atom and a bromine atom are preferred. In each polymer, all of Xs are generally the same, while at least part of them may be different.

n is generally preferably 2 to 5,000.

The polymer of the formula (1) preferably has a number average molecular weight $M_n$ of approximately 1,000 to 1,000,000.

The polymer of the formula (1) is preferably synthesized by reacting a diamine compound with a dihalogen compound. When a dihalogen compound is used, the synthesized polymer has an increased molecular weight, and the humidity resistance improves.

The scheme of the above synthesis reaction is represented as an expression (2).

Expression (2)

$$\begin{array}{c} R_1 \quad R_3 \\ \diagdown \quad \diagup \\ N-A-N \\ \diagup \quad \diagdown \\ R_2 \quad R_4 \end{array} + X-B-X \longrightarrow$$

$$-B-(N^+-A-N^+-B)_n^- \\ \quad | \quad \quad | \\ \quad R_2X^- \quad R_4X^-$$

The above synthesis reaction is preferably carried out under conditions where the amount of the dihalogen compound per mole of the diamine compound is 1.0 to 2.0 mol.

The above synthesis reaction is carried out in a nonaqueous solvent such as methanol, ethanol, isopropanol, methoxyethanol or 2-ethoxyethanol at a temperature between a reflux temperature and about 100° C. for approximately 5 to 100 hours.

Then, the reaction mixture is dropwise added to a solvent such as ethyl acetate to form a precipitate, and the precipitate is recovered by filtration, to obtain an end product.

The polymer of the formula (1) is generally obtained as a mixture of an oligomer having a polymerization degree n of approximately 2 to 20 with a polymer having a polymerization degree n of over 20.

The diamine compound and the dihalogen compound are not specially limited so long as they permit a reaction according to the scheme represented by the expression (2).

Specifically, the diamine compound is preferably any one of the following A-1 to A-18, and the dihalogen compound is preferably any one of the following B-1 to B-17.

A-1

Me\\N—(CH$_2$)$_2$—N/Me
Me/  \\Me

N, N, N', N'-tetramethyldiaminoethane

A-2

Et\\N—(CH$_2$)$_3$—N/Et
Et/  \\Et

N, N, N', N'-tetraethyl-1,3-propanediamine

A-3

Me\\N—CH$_2$CH=CH—CH$_2$—N/Me
Me/  \\Me

N, N, N', N'-tetramethyl-2-butene-1,4-diamine

A-4

Me\\N—⟨phenyl⟩—⟨phenyl⟩—N/Me
Me/  \\Me

N, N, N', N'-tetramethylbenzidine

A-5

Me\\N—CH$_2$—CH—CH$_2$—N/Me
Me/      |      \\Me
         OH 1,3-bis(dimethylamine)-2-propanol

A-6

Me\\  Me         Me
  N—CH—CH$_2$—CH$_2$—N/
Me/              \\Me

N, N, N', N'-tetramethyl-1,3-diaminobutane

A-7

⟨pyridyl⟩—CH$_2$—CH$_2$—CH$_2$—⟨pyridyl⟩

1,3-di(4-pyridyl)propane

A-8

⟨N—N bicyclic structure⟩

1,4-diazabicyclo[2.2.2]octane (triethylenediamine)

A-9

Me—N⟨piperazine⟩N—Me

N, N'-dimethylpiperazine

A-10

Me—N⟨piperidyl⟩—CH$_2$CH$_2$CH$_2$—⟨piperidyl⟩N—Me

N, N'-dimethyl-1,3-di-4-piperidylpropane

A-11

⟨pyrazine⟩ pyrazine

-continued

pyrazineamide

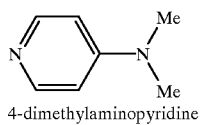
4-dimethylaminopyridine

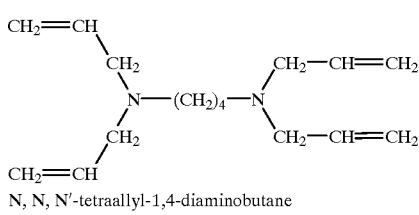
N, N, N'-tetraallyl-1,4-diaminobutane

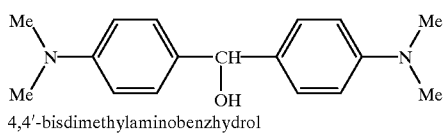
4,4'-bisdimethylaminobenzhydrol

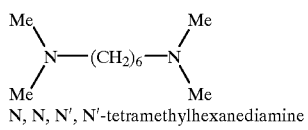
N, N, N', N'-tetramethylhexanediamine

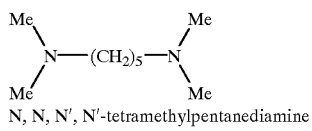
N, N, N', N'-tetramethylpentanediamine

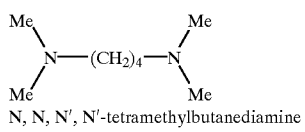
N, N, N', N'-tetramethylbutanediamine

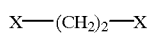 B-1

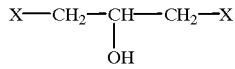 B-2

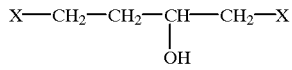 B-3

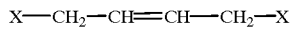 B-4

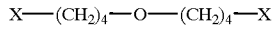 B-5

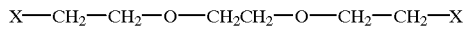 B-6

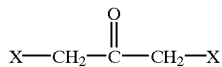 B-7

-continued

A-12

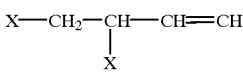 B-8

A-13

 B-9

A-14

X—(CH$_2$)$_3$—X  B-10

X—(CH$_2$)$_4$—X  B-11

X—(CH$_2$)$_5$—X  B-12

X—(CH$_2$)$_6$—X  B-13

X—(CH$_2$)$_9$—X  B-14

A-15

X—(CH$_2$)$_{10}$—X  B-15

X—(CH$_2$)$_{12}$—X  B-16

A-16

X—(CH$_2$)$_{16}$—X  B-17

In B-1 to B-17, X is as defined before, while it is particularly preferably an iodine atom or a bromine atom.

Of the above-described diamine compounds, cyclic amines, 1,4-diazabicyclo[2.2.2]octane (triethylenediamine) of A-8 in particular, are preferred since the solid electrolyte shows a high ion conductivity and has high mechanical strength and high humidity resistance.

A-17

Examples of the polymer of the formula (1) will be shown below as polymers obtained from combinations of the above diamine compounds and dihalogen compounds. Parenthesized values show molar ratios.

(1) Polymer obtained from a combination of A-16/B-10 (50/50)

(2) Polymer obtained from a combination of A-8/B-12/B-10 (50/48/2)

A-18

(3) Polymer obtained from a combination of A-8/B-13/B-10 (50/48/2)

(4) Polymer obtained from a combination of A-8/B-15/B-10 (50/48/2)

(5) Polymer obtained from a combination of A-16/B-2 (50/50)

(6) Polymer obtained from a combination of A-7/B-10 (50/50)

(7) Polymer obtained from a combination of A-2/B-10 (50/50)

(8) Polymer obtained from a combination of A-9/B-10 (50/50)

(9) Polymer obtained from a combination of A-16/B-9 (50/50)

(10) Polymer obtained from a combination of A-3/A-8/B-10 (2/48/50)

(11) Polymer obtained from a combination of A-14/A-16/B-17 (49/1/50)

(12) Polymer obtained from a combination of A-11/B-16 (50/50)

(13) Polymer obtained from a combination of A-6/B-4/B-15 (50/47/3)

(14) Polymer obtained from a combination of A-11/B-6 (50/50)

(15) Polymer obtained from a combination of A-13/B-3 (50/50)

(16) Polymer obtained from a combination of A-10/B-15 (50/50)
(17) Polymer obtained from a combination of A-15/B-16 (50/50)
(18) Polymer obtained from a combination of A-4/B-10 (50/50)
(19) Polymer obtained from a combination of A-10/B-12/B-10 (50/48/2)
(20) Polymer obtained from a combination of A-8/B-2 (50/50)
(21) Polymer obtained from a combination of A-7/A-16/B-10 (15/35/50)
(22) Polymer obtained from a combination of A-8/A-16/B-10 (15/35/50)
(23) Polymer obtained from a combination of A-9/A-16/B-10 (15/35/50)
(24) Polymer obtained from a combination of A-10/A-16/B-10 (15/35/50)
(25) Polymer obtained from a combination of A-8/B-13 (50/50)
(26) Polymer obtained from a combination of A-8/A-10/B-13 (15/35/50)
(27) Polymer obtained from a combination of A-8/B-13/B-10 (50/40/10)
(28) Polymer obtained from a combination of A-8/B-13/B-2 (50/40/10)
(29) Polymer obtained from a combination of A-9/B-13 (50/50)
(30) Polymer obtained from a combination of A-8/A-9/B-13 (25/25/50)
(31) Polymer obtained from a combination of A-9/A-10/B-13 (25/25/50)
(32) Polymer obtained from a combination of A-8/B-10 (50/50)

In the present invention, polymers of the formula (1) are generally used alone, while two or more polymers of the formula (1) may be used in combination.

A material for Solid Electrolyte (monomer)

Besides the above polymers, the compound having an ammonium ion portion, used for the above solid electrolyte, can be preferably selected from alkylammonium halide, arylammonium halide or nitrogen-containing cyclic ammonium halide. Examples thereof are compounds including diammonium dihalide and monoammonium halide.

The ammonium ion portion of the monomer compound having an ammonium ion portion preferably includes the following.

1. Alkylammonium
1-1 Methylammonium
1-2 Ethylammonium
1-3 Trimethylammonium
1-4 Diethylammonium
1-5 Diethylmethylammonium
1-6 Triethylammonium
1-7 Ethyltrimethylammonium
1-8 Diethyldimethylammonium
1-9 Trimethylisopropylammonium
1-10 Trimethylpropylammonium
1-11 Triethylmethylammonium
1-12 Tetraethylammonium
1-13 Diethylmethylisopropylanmonium
1-14 Triethylpropylammonium
1-15 Butyldiethylmethylammonium
1-16 Butyltriethylammonium
1-17 Methyltripropylammonium
1-18 Tetrapropylammonium
1-19 Tributylmethylaimonium
1-20 Butyltripropylammonium
1-21 Tributylethylammonium
1-22 Tetrabutylammonium
1-23 Hexadecyltrimethylanmonium 2. Nitrogen-containing saturated cyclic ammonium
2-1 Pyrrolidinium
2-2 Piperidinium
2-3 1-Methylpiperidinium
2-4 1-Methylpyrrolidinium
2-5 1,1-Dimethylpyrrolidinium
2-6 Quinuclidinium
2-7 1-Methylquinuclidinium
2-8 1,1-Dimethylpiperidinium
2-9 N-Methylquinuclidinium
2-10 5-Azoniaspiro[4.4]nonane
2-11 5-Azoniaspiro[4.5]decane
2-12 6-Azoniaspiro[5.5]undecane
2-13 1-Butyl-1-methylpiperidinium
2-14 Methylhexamethylenetetramminium
2-15 N,N'-Dimethylpiperazinium
2-16 Ethylhexamethylenetetramminium
2-17 Propylhexamethylenetetramminium
2-18 Butylhexamethylenetetramminium
2-19 Isobutylhexamethylenetetramminium
2-20 N,N'-Diethylpiperazinium 3. Nitrogen-containing unsaturated cyclic ammonium
3-1 Pyridinium
3-2 3-Methylpyridinium
3-3 1-Methylpyridinium
3-4 1,4-Dimethylpyridinium
3-5 3,5-Dimethylpyridinium
3-6 2,6-Dimethylpyridinium
3-7 1,2,6-Trimethylpyridinium
3-8 3,4,6-Trimethylpyridinium
3-9 1,3,5-Trimethylpyridinium
3-10 Quinolinium
3-11 1,2,4,6-Tetramethylpyridinium
3-12 1,2,3,6-Tetramethylpyridinium
3-13 1-Methylquinolinium
3-14 1-Methyl-1,2,3,4-tetrahydroquinolinium
3-15 2-Methyl-1,2,3,4-tetrahydroquinolinium
3-16 1-Ethylquinolinium
3-17 1,2-Dimethylquinolinium
3-18 1,2-Dimethyl-1,2,3,4-tetrahydroquinolinium
3-19 1,1-Dimethyl-1,2,3,4-tetrahydroquinolinium
3-20 2,2-Dimethyl-1,2,3,4-tetrahydroisoquinolinium
3-21 1-Ethyl-2-methylquinolinium
3-22 1-Ethyl-2,6-dimethylquinolinium
3-23 N-Methylphenanthridinium 4. Saturated carbocyclic ammonium
4-1 Cyclopentylammonium
4-2 Cyclopropyltrimethylammonium
4-3 Cyclohexylammonium
4-4 Cyclopentyltrimethylammonium 4-5 Cyclohexyltrimethylammonium 4-6 Butylcyclohexyldimethylammonium 4-7 Adamantyltrimethylammonium 5. Unsaturated hydrocarbon ammonium 5-1 4-Methyl-4-azoniacyclohexene 5-2 Allyltrimethylammonium 5-3 4,4-Dimethyl-4-azoniacyclohexene 6. Arylammonium 6-1 Phenylainmonium 6-2 Trimethylphenylammonium 6-3 Ethyldimethylphenylammonium 7. Benzylammonium 7-1 Banzylammonium 7-2 Benzyltrimethylammonium 7-3 1-Benzylpyridinium 7-4 1-Benzylquinolinium Further, examples of the compound having an ammonium ion portion preferably include the following compounds.

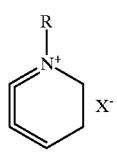
N-1

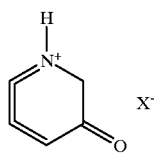
N-2

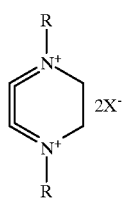
N-3

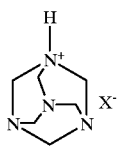
N-4

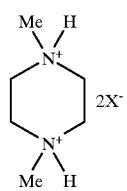
N-5

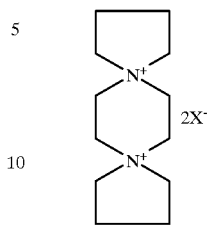
N-6

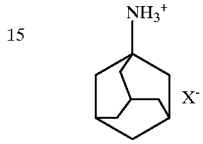
N-7

In the above N-1 to N-7, X is a halogen atom, preferably a chlorine atom, a bromine atom or an iodine atom, more preferably an iodine atom or a bromine atom. In the above N-1, R is a hydrogen atom or methyl. In the above N-3, R is a hydrogen atom, methyl, ethyl or propyl, and two Rs are generally the same, while they may be different from each other.

Each of the above monomers can be synthesized from an amine compound and a halogen compound according to a conventional method.

Metal Halide

The metal halide used for the preparation of the solid electrolyte preferably includes Ag or Cu halides. Of these, a chloride, a bromide or an iodide is preferred, and a bromide or an iodide is more preferred. A metal in the metal halide exhibits conductivity in the solid electrolyte, and when Ag or Cu is used as the above metal, the solid electrolyte is formed as one having high stability.

Production of Solid Electrolyte

A solid electrolyte is produced by heat-treating the above solid electrolyte materials such as the above polymer or monomer and the above metal halide. Specifically, a solid electrolyte material and a metal halide are fully mixed first, then, preferably, the mixture is shaped, and then the mixture or the shaped mixture is allowed to react under heat.

The mixing ratio of solid electrolyte material and the metal halide differs depending upon compounds used. Generally, however, the amount of the metal halide per mole of ammonium group of the solid electrolyte material is preferably 4 to 10 mol.

When the above mixture in the state of a powder is allowed to react under heat, it is difficult to obtain a high conductivity. It is therefore preferred to shape a powder of the mixture. The shaping pressure therefor is preferably at least 400 kgf/cm$^2$, more preferably at least 700 gf/cm$^2$.

Although differing depending upon a solid electrolyte material, generally, the temperature range for the heat treatment is preferably 100 to 220° C., more preferably 120 to 190° C. When the temperature for the heat treatment is too low, the reaction does not proceed well, and the heat treatment takes too long a time for attaining a sufficient ion conductivity. When the temperature for the heat treatment is too high, the solid electrolyte material is liable to undergo thermal decomposition, and in addition thereto, it is liable to be difficult to obtain sufficient mechanical strength. The time period for the heat treatment is generally approximately 8 to 20 hours. The heat treatment may be carried out in atmosphere in some cases, while it is generally preferred to decrease an amount of oxygen in an ambient atmosphere by pressure reduction. Generally, when atmospheric pressure is reduced, the pressure is preferably approximately $10^{-2}$ Torr or lower. When the pressure is too high, undesirably, organic substance causes oxidation with residual oxygen to be deteriorated. When the heat treatment is carried out in an atmosphere of inert gas such as Ar or $N_2$, no particular pressure reduction is required.

After the heat treatment, preferably, a treatment product is pulverized to a fine powder and the fine power is re-shaped. The shaping pressure therefor is preferably at least 400 kgf/cm², more preferably 700 kgf/cm². When the shaping pressure is too low, a shaped product is fragile so that it is difficult to attain a practical strength. When a monomer containing a linear alkyl group having a smaller number of carbon atoms is used as a solid electrolyte material, particularly, the above tendency appears to a great degree. When a polymer, preferably a polymer from 1,4-diazabicyclo [2.2.2.]octane (triethylenediamine) and a dihalogen compound, is used as a solid electrolyte material, there is no problem on fragility. Even in this case, however, it is preferred to set the shaping pressure at a high level for obtaining high mechanical strength. For obtaining a shaped product having a high density, it is preferred to keep the inside of a mold in a state of reduced pressure during the shaping.

Detection Electrode

As a material for the detection electrode, metal carbonate which forms a dissociation equilibrium with carbon dioxide is used. Specifically, silver carbonate or copper carbonate is preferred. One of these can be selected depending upon kinds of movable ion of the solid electrolyte. The above carbonates have characteristic features that they are excellent in humidity resistance and show a relatively high ion conductivity at room temperature as compared with conventional sodium carbonate used as a detection electrode material. Therefore, a sufficient electromotive force is obtained at room temperature, and a sufficiently high responsiveness is attained.

When, for example, silver carbonate is used as a detection electrode material, the reaction to take place on the detection electrode side is considered to be as follows.

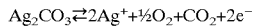

As a material for the detection electrode, it is preferred to use at least two metal carbonates which form dissociation equilibrium with carbon dioxide. Specifically preferably, silver carbonate or copper carbonate is used as a main component, and a metal carbonate, preferably an alkali metal carbonate, is mixed therewith. In this case, a change in the electromotive force on the basis of a change in the concentration of carbon dioxide increases. The alkali metal carbonate to be added is not specially limited, and any alkali metal carbonate shows an effect, while lithium carbonate is preferred. The content thereof is not specially limited, while it is preferably 50% by weight or less, particularly preferably in the vicinity of 5 to 10% by weight. One metal carbonate or at least two metal carbonates may be added. When at least two metal carbonates are added, the total amount thereof is preferably in the above range.

When, for example, silver carbonate and lithium carbonate are used as a detection electrode material, the reaction taking place on the detection electrode side is considered to be mainly a dissociation reaction of the above silver carbonate. During the above reaction, it is considered that the added alkali metal carbonate, lithium carbonate in this case, is dissociated to a slight extent. Since, however, the kind of movable ion of the solid electrolyte is silver, the dissociation thereof cannot constitute a main reaction. It is not clear why the change in the electromotive force on the basis of a change in carbon dioxide is increased by the addition of the alkali metal carbonate, while it is considered that when a substance that can easily undergo dissociation is added, the reaction proceeds like an ion-exchange reaction, so that silver carbonate is dissociated to a greater extent. When the silver carbonate as a main component is replaced with copper carbonate, the reaction on the detection electrode side is also considered to be a reaction in which copper carbonate is dissociated.

The method of mixing the metal carbonates is not specially limited. Generally, silver carbonate or copper carbonate which constitutes a main component and the additional alkali metal carbonate are milled and mixed in a small-sized ball mill, etc., for approximately several hours to 1 day. In this case, ethanol, acetone, etc., may be added.

The silver carbonate as a material is preferably $Ag_2CO_3$. The copper carbonate is preferably $Cu(CO_3).Cu(OH)_2$ or $2Cu(CO_3).Cu(OH)_2$. The alkali metal salt to be added, e.g., lithium carbonate, is preferably $Li_2CO_3$. These materials may be deviated in stoichiometric compositions to some extent.

The metal carbonate used for the detection electrode preferably has a particle diameter of approximately 1 to 100 μm.

In addition to the metal carbonate, the detection electrode may contain a binder for increasing the element strength. The binder can be selected from generally used binders such as polyvinyl alcohol, polyvinyl butyral, polyethylene glycol, methyl cellulose, ethyl cellulose, etc., and in addition to these, it can be also selected from a phenolic resin which is a thermosetting resin, an aniline resin, a silicon resin, an unsaturated polyester resin, an epoxy resin, a polyethylene resin, a polypropylene resin and a polystyrene resin. Of these, ethyl cellulose, acetyl cellulose and polyvinyl acetate which are hydrophobic binders are preferred. The content of the binder is preferably 1 wt % or less based on the detection electrode.

The method of shaping the detection electrode is not specially limited. Generally, the detection electrode is shaped by laminating a detection electrode material powder and the above solid electrolyte and then pressing the resultant laminate. In this case, preferably, an electrically conductive mesh of Pt, Ni, etc., is placed in or on the detection electrode material powder in advance, to form a structure in which a lead wire is to be connected to the mesh. An electrically conductive material other than the mesh may be used so long as it does not hinder the transmission of gases. For example, a paste which is a mixture of the detection electrode material powder and a resin may be applied, to form the detection electrode. In this case, preferably, a solvent having no compatibility or a foaming agent is incorporated in advance, and the paste is applied and then dried to form a porous detection electrode.

Reference Electrode

When the movable ion is Ag ion, a silver/silver chloride electrode often used as a reference electrode in a solution system can be used as a stable reference electrode in the sensor of the present invention. The electrode reaction in this case is considered as below.

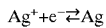

When silver carbonate is used in the detection electrode, the total electrode reaction is considered as below.

$$Ag_2CO_3 \rightleftarrows 2Ag + \tfrac{1}{2}O_2 + CO_2$$

When the silver/silver chloride electrode is not used, it is assumed that silver oxide is formed in the reference electrode interface. In this case, the influence of an oxygen concentration can be prevented by using an oxygen ion conductive solid electrolyte in combination. Since, however, the oxygen ion conductive solid electrolyte is generally a yttrium stabilized zirconia or the like, a high temperature is required to attain the conductivity, which is unsuitable in the present invention. When the silver/silver chloride electrode is not used, the operation at room temperature can be made by the use of a reference electrode which itself contains silver oxide, specifically, a silver/silver oxide electrode. The electrode reaction in this case is considered as below.

$$2Ag^+ + \tfrac{1}{2}O_2 + 2e^- \rightleftarrows Ag_2O$$

The total electrode reaction in this case is considered as below.

$$Ag_2CO_3 \rightleftarrows Ag_2O + CO_2$$

When the movable ion is Cu ion, the operation at room temperature can be attained by the use of a reference electrode containing copper oxide, specifically, a copper/copper oxide electrode for the same reason. The electrode reaction in this case is considered as below.

$$CuCO_3 \cdot Cu(OH)_2 \rightleftarrows Cu_2^+ + \tfrac{1}{2}O_2 + CO_2 + 2e^- + Cu(OH)_2$$
$$Cu^{2+} + \tfrac{1}{2}O_2 + 2e^- \rightleftarrows CuO$$

The total electrode reaction in this case is considered as below.

$$CuCO_3 \cdot Cu(OH)_2 \rightleftarrows CuO + CO_2 + Cu(OH)_2$$

The method of forming the reference electrode is not specially limited, while it is preferred to use, e.g., the following method. In the case of a silver/silver chloride electrode and a silver/silver oxide electrode, a silver powder and a silver chloride or a silver oxide powder are mixed, the mixture and a solid electrolyte material are laminated, and then, the these are pressed at the same time to form the reference electrode. Otherwise, a silver paste and a silver chloride or silver oxide powder are mixed to prepare a silver/silver chloride paste or a silver/silver oxide paste, the paste is applied together with a Pt or Ni mesh and then the applied paste is hardened under heat, whereby the reference electrode can be formed. Further, when the reference electrode is a copper/copper oxide electrode, a mixture of a copper powder with a copper oxide powder and a solid electrolyte material are laminated and these are pressed at the same time. Otherwise, a copper paste and copper oxide can be used in place of the silver paste and the silver oxide used for the formation of the above silver/silver oxide electrode. The temperature for the hardening under heat is generally approximately 80 to 200° C., and unlike a ceramic material, firing at a high temperature of around 1,000° C. is not required, which makes the sensor production easy and also serves to save energy.

Structure of Sensor and Function in Measurement

FIG. 1 shows an example of configuration of the carbon dioxide sensor of the present invention. This carbon dioxide sensor 1 has a structure in which a reference electrode 3, a solid electrolyte 4 and a detection electrode 5 are consecutively laminated. Inside the reference electrode 3 and inside the detection electrode 5 are electrically conductive meshes 31 and 51, respectively. A lead wire 31 and a lead wire 51 are led out from the meshes and connected to a potentiometer. The carbon dioxide sensor of the present invention preferably has a structure in which surfaces other than the detection electrode surface are not in contact with an atmosphere to be measured, for preventing an influence caused by humidity. For this reason, preferably, surfaces other the detection electrode surface are provided with a coating formed of a gas-impermeable material. A coating formed of a gas-impermeable material such as vinyl chloride, eval (ethylene-vinyl alcohol copolymer), ionomer or PVA, or a laminate of the above coating and an Al deposition film is preferred. As a specific structure, it is preferred to provide a structure in which surfaces other than the surface of the detection electrode 5 are covered with a container 2 formed of a gas-impermeable material as shown in Figure.

In the shown example, the detection electrode and the reference electrode are disposed so as to be opposed to each other with the solid electrolyte therebetween, while these two electrode may be disposed on one surface of the solid electrolyte. A structure in which both the electrodes are formed on one surface of the solid electrolyte by a screen printing method, etc., is highly efficient in view of productivity.

The dimensions of the carbon dioxide sensor of the present invention are not specially limited. When the surface on which the detection electrode is to be formed is the upper surface of the solid electrolyte, generally, the thickness of the solid electrolyte is approximately 1 $\mu$m to 1 mm, and the area of upper surface of the solid electrolyte is approximately 1 to 100 mm$^2$. Further, the detection electrode has a thickness of approximately 1 $\mu$m to 1 mm and an area of approximately 1 to 50 mm$^2$. Further, the reference electrode has a thickness of approximately 10 $\mu$m to 1 mm and an area of approximately 1 to 50 mm$_2$.

In addition to the carbon dioxide sensor shown in FIG. 1, the carbon dioxide sensor of the present invention preferably has a temperature detection element for detecting a temperature of the above carbon dioxide sensor and/or a humidity detection element for detecting a humidity around the above carbon dioxide sensor.

Temperature Detection Element

The element for detecting a temperature in the present invention is not specially limited, while it is preferably selected from a resistor type, a thermistor type or a diode type, for automatically correcting an output of the carbon dioxide sensor. The resistor type is highly reliable since its linear characteristic is excellent and its aged deterioration is small. Since the resistor type differs in characteristic to a great extent depending upon materials used, careful selection is required. The material that can be used includes platinum, nickel and copper, while copper is preferred since it is inexpensive, has a high temperature coefficient and has uniform characteristics. The thermistor type and the diode type are highly sensitive and are preferred for decreasing the element in size.

The disposition of the element is not specially limited, while it is preferred to dispose the element on a plane on which the carbon dioxide sensor is disposed or to dispose the element directly in contact with the carbon dioxide sensor.

Humidity Detection Element

The element for detecting a humidity in the present invention is not specially limited, while it is preferably selected from an electric resistor type, electric capacitor type, concentration cell type or thermistor type humidity sensor in view of a size and a cost. Of these, the electric resistor type uses a porous ceramic and a high-molecular-weight polymer and is suitable for continuous humidity measurement at room temperature, and it is the most preferred in view of accuracy and a cost.

The disposition of the element is not specially limited, while it is preferred to dispose the element on a plane where the carbon dioxide sensor is disposed in view of humidity measuring accuracy.

Structure of Sensor and Function During Measurement

Figure 2:
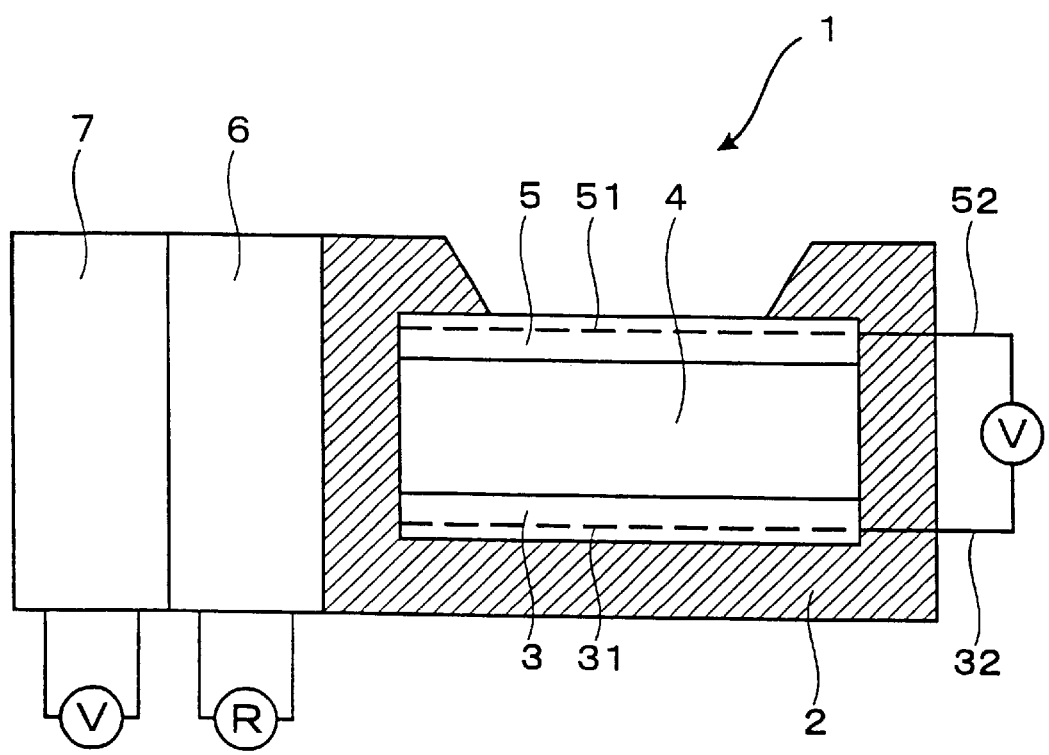
FIG. 2 is a cross-sectional view showing a configuration of a carbon dioxide sensor having a temperature detection element and a humidity detection element, provided by the present invention.
Figure 3:
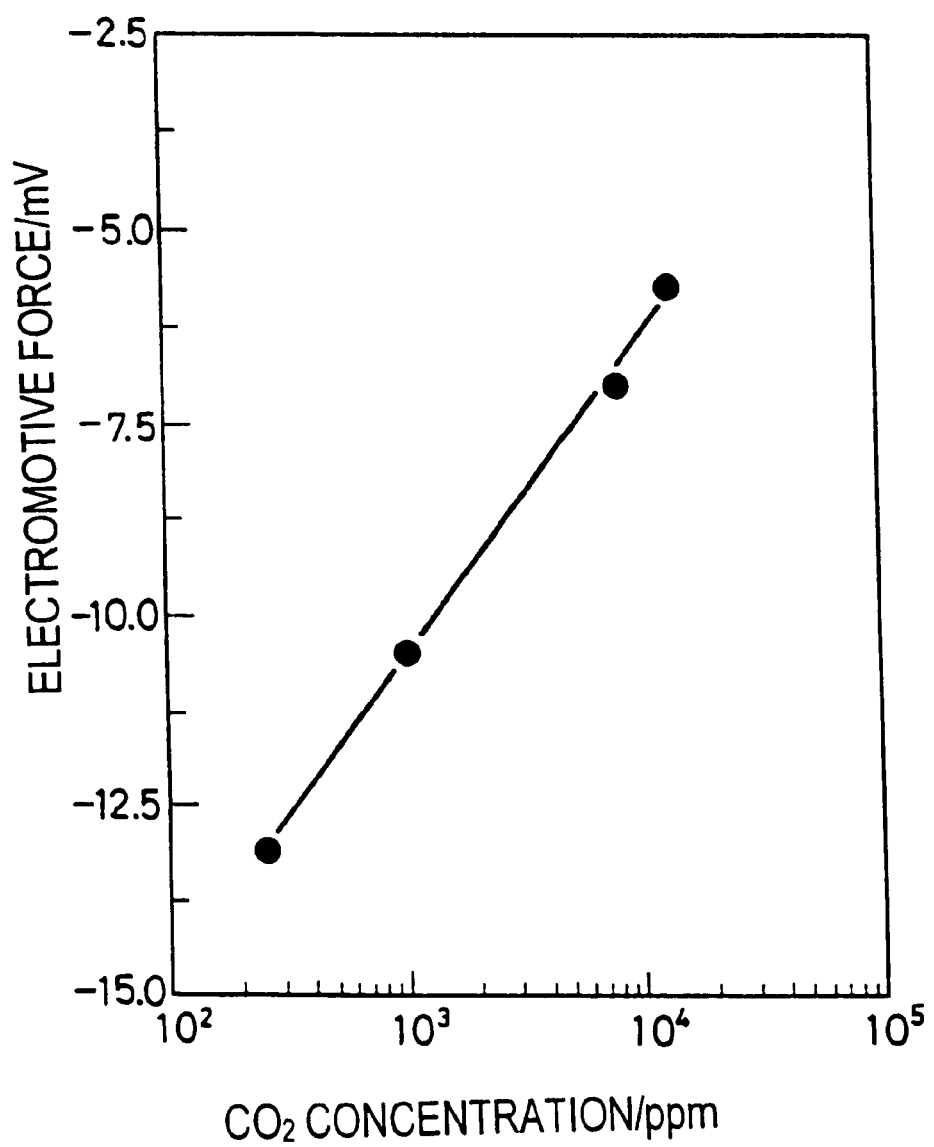
FIG. 3 is a graph showing a relationship between a carbon dioxide concentration and the electromotive force of a sensor D.
Figure 4:
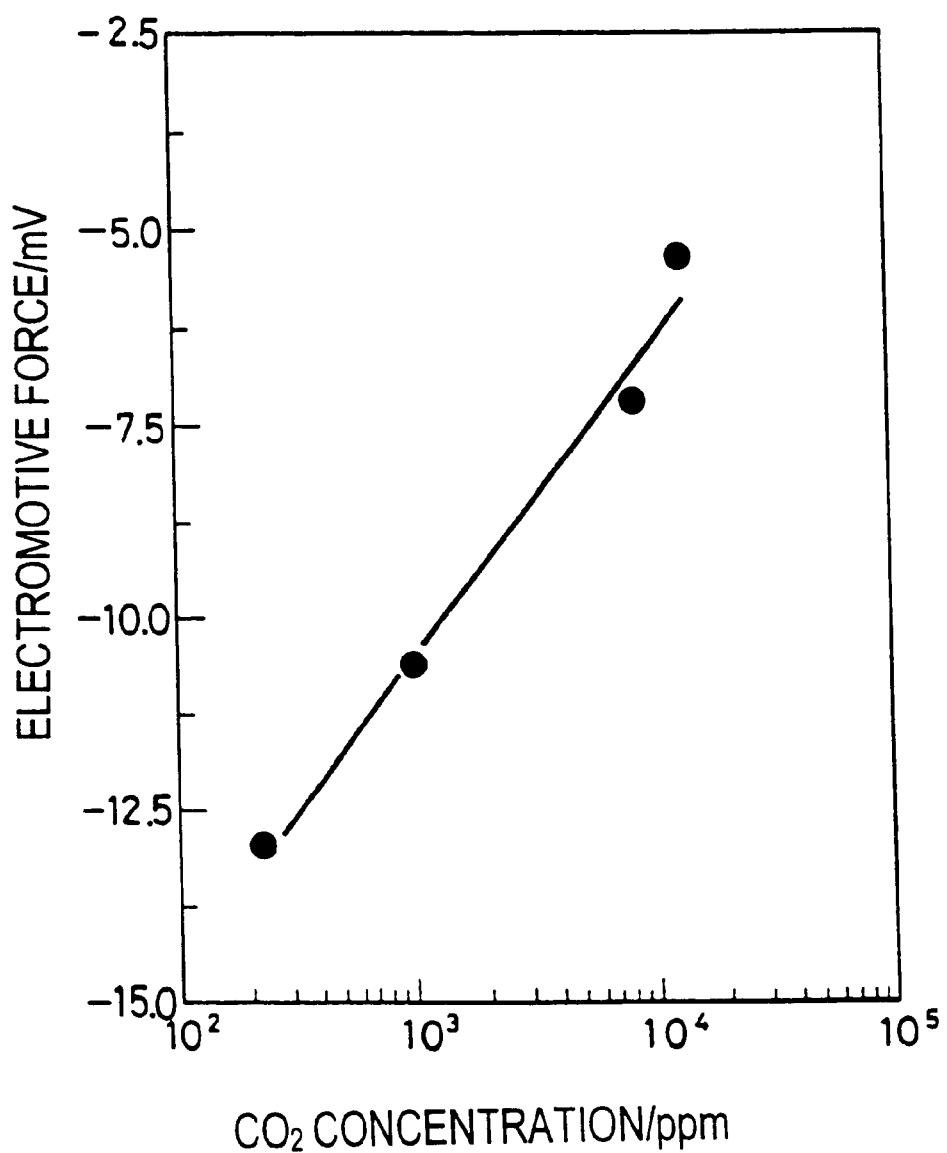
FIG. 4 is a graph showing a relationship between a carbon dioxide concentration and the electromotive force of a sensor E.
Figure 5:
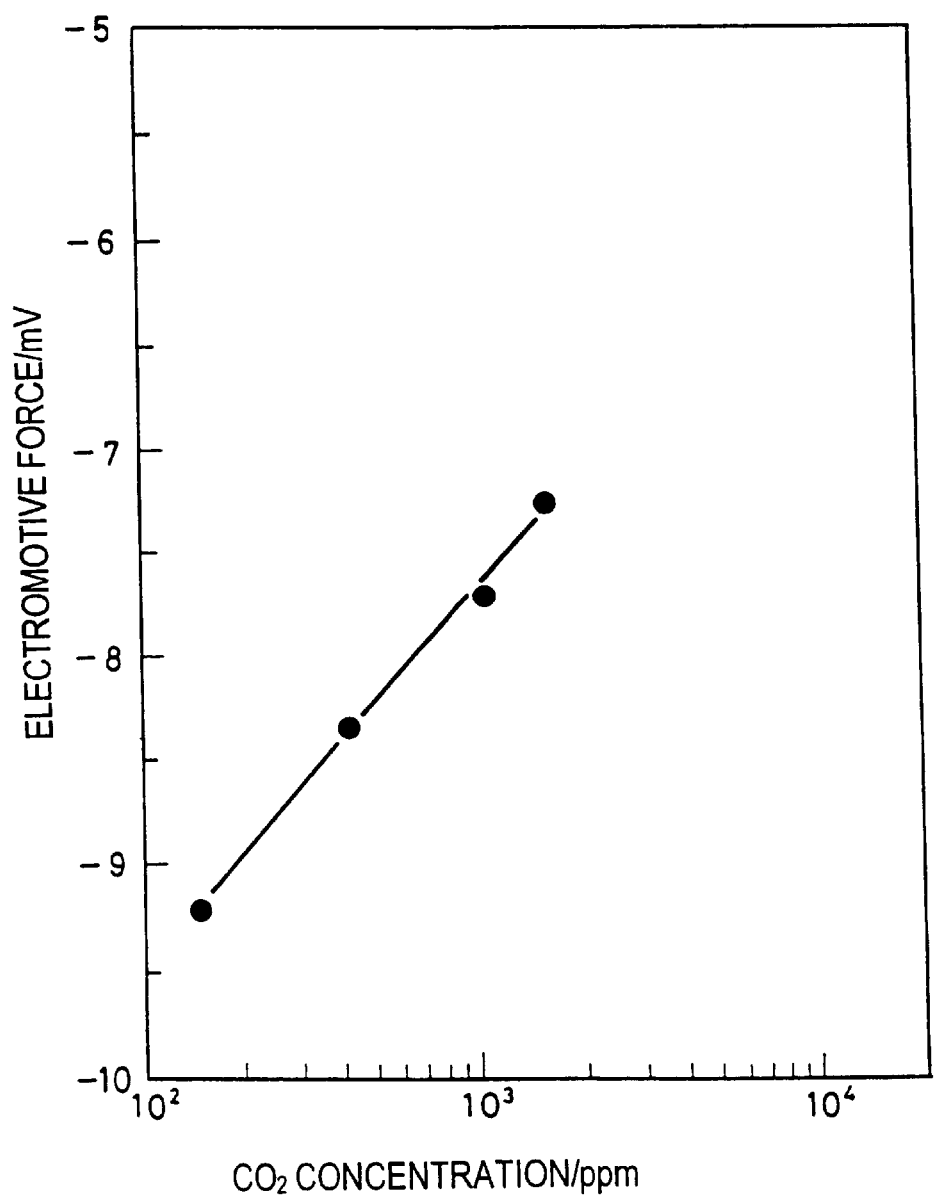
FIG. 5 is a graph showing a relationship between a carbon dioxide concentration and the electromotive force of a sensor I.
Figure 6:
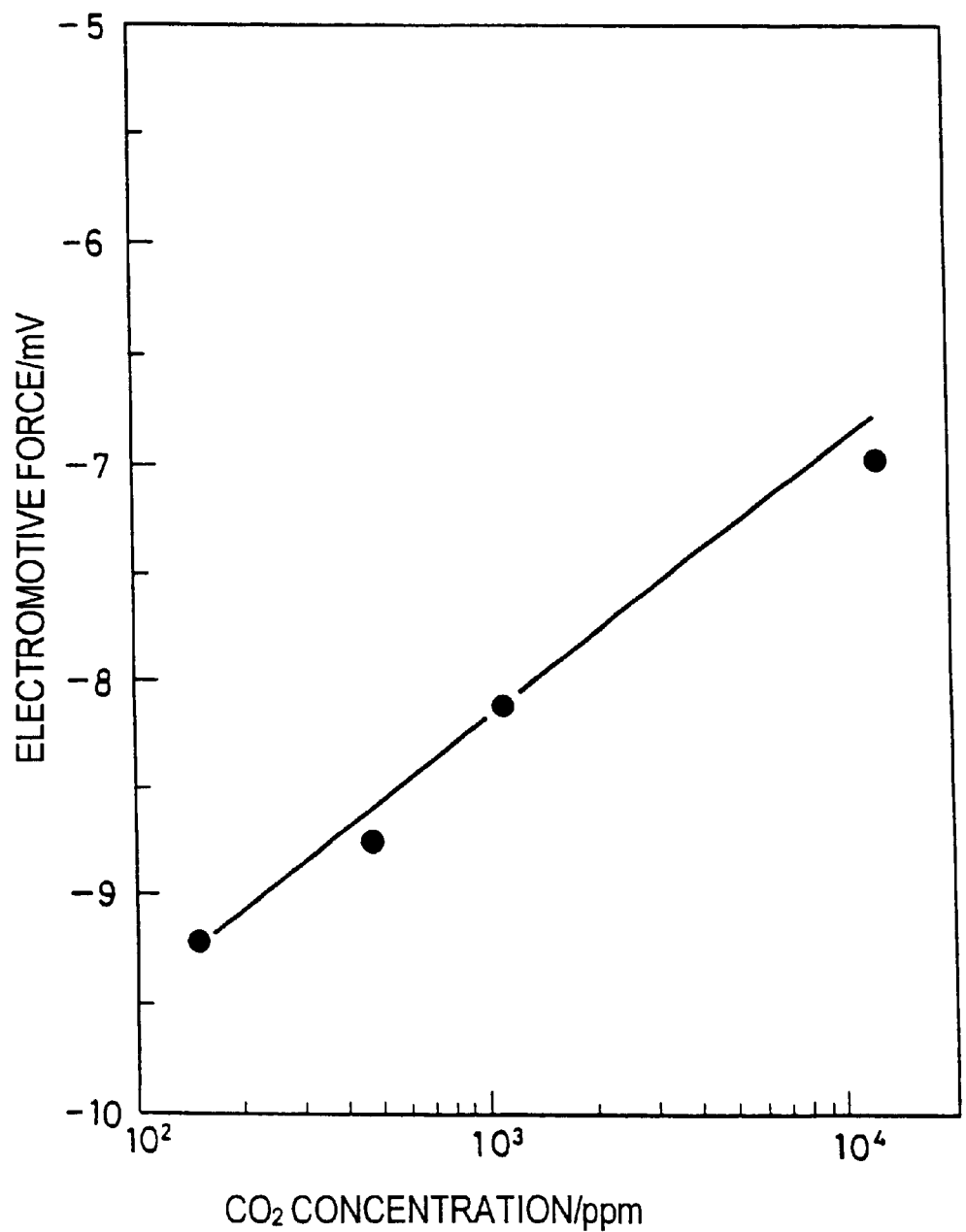
FIG. 6 is a graph showing a relationship between a carbon dioxide concentration and the electromotive force of a sensor Q.

FIG. 2 shows a configuration example of a carbon dioxide sensor device having a temperature detection element and a humidity detection element. A carbon dioxide sensor 1 is similar to the sensor shown in FIG. 1 and has a structure in which a reference electrode 3, a solid electrolyte 4 and a detection electrode 5 are consecutively laminated. Inside the reference electrode 3 and inside the detection electrode 5 are electrically conductive meshes 31 and 51, respectively, and a lead wire 31 and a lead wire 51 are led out from the meshes and connected to a potentiometer.

A temperature detection element 6 and a humidity detection element 7 are provided adjacent to the above carbon dioxide sensor 1 and on the same place as that on which the carbon dioxide sensor 1 is disposed. In the shown example, the temperature detection element 6 is an element for measuring a temperature by utilizing a resistance change of a copper wire, and a resistance value is referred to a value calibrated in advance, to obtain temperature data. The humidity detection element 7 outputs a humidity as a voltage and has a voltmeter in an output terminal to obtain humidity data.

In the above carbon dioxide sensor device, the carbon dioxide sensor 1 measures an electromotive force, and at the same time, the temperature detection element 6 detects a temperature and the humidity detection element 8 detects a humidity. The electromotive force is corrected with regard to the temperature and the humidity, and a carbon dioxide concentration is determined on the basis of the corrected electromotive force. When an electromotive force is corrected as described above, carbon dioxide to be measured can be accurately measured for a concentration, particularly, at room temperature.

The electromotive force is according to the expression of Nernst, $$E = E_0 - (RT/2F) \ln(aAg_2O \cdot PCO_2)$$

the electromotive force has a linear relationship with the temperature of the device. In the above expression, E is an electromotive force, $E_0$ is a constant, R is a gas constant, T is an absolute temperature, F is Faraday constant, $2Ag_2O$ is an activity of $Ag_2O$, and $PCO_2$ is a partial pressure of carbon dioxide gas. For correcting the electromotive force, the above theoretical expression can be directly used, or a relational expression obtained on the basis of preliminary actual measurements can be used. Since values may differ depending upon characteristics of sensors, it is preferred to use an expression obtained on the basis of actual measurements.

The relational expression between the electromotive force and the temperature can be experimentally determined while the temperature is changed at a constant carbon dioxide concentration and at a constant humidity.

On the other hand, the electromotive force and the humidity have no theoretical relational expression unlike the temperature. When measured actually, however, the electromotive force and the humidity have a linear relationship like the temperature. The relational expression of the electromotive force and the humidity is determined on the basis of preliminary actual measurements, and the electromotive force is corrected by utilizing the expression.

The relational expression between the electromotive force and the humidity can be experimentally determined while the humidity is changed at a constant carbon dioxide concentration and at a constant temperature.

The electromotive force can be automatically corrected with expressions and conversion tables computerized in advance.

EXAMPLES

Example 1

Synthesis of Solid Electrolyte Materials

An amine compound and a halide was combined as shown in the following Table 1, and the combination was dissolved in ethanol. Then, the mixture was stirred with a stirrer at room temperature or under heat for 1 to 3 days. Then, a formed white precipitate was recovered by filtration, washed with a small amount of ethanol, then washed with ether and then dried under reduced pressure to obtain a solid electrolyte material as a polymer or a monomer. The yield in each case was at least 90%. Before used, the solid electrolyte material was purified by recrystallization from ethanol as required. Concerning the mixing ratio of the amine compound and the halide, equimolar amounts of these were used for polymers, and a large excess of halides were used for monomers.

TABLE 1

| Solid electrolyte No. | State | Amine compound | Halogen compound |
|---|---|---|---|
| 1 | monomer | pyridine | methyl iodide |
| 2 | monomer | piperazine | ethyl iodide |
| 3 | monomer | 1,4-diazabicyclo-[2.2.2]octane (triethylenediamine) | propyl iodide |
| 4 | polymer | 1,4-diazabicyclo-[2.2.2]octane (triethylenediamine) | 1,3-dibromo-propane |
| 5 | monomer | hexamethylenetetramine | methyl iodide |
| 6 | monomer | quinuclidine | methyl bromide |
| 7 | polymer | piperazine | 1,3-dibromo-propane |

Synthesis of Solid Electrolyte

The synthesized solid electrolyte material and a metal halide were fully mixed in an agate mortar, and the mixture was pressed at 700 kgf/cm$^2$ to give a shaped material in the form of pellets. The shaped material was allowed to react by heat-treating it under reduced pressure ($1 \times 10^{-3}$ Torr). The heat-treated pellets was blackish brown or greenish brown. Table 2 shows combinations of solid electrolytes and metal halides and heat-treatment temperatures (reaction temperatures) for the combinations.

The heat-treated pellets were milled and the milled product was again shaped under pressure at 700 kgf/cm$^2$, to show that most of them turned black.

The above-obtained solid electrolytes were measured for ion conductivity (electric conductivity) with an AC impedance meter. Table 2 shows the results.

TABLE 2

| Solid Electrolyte | Solid electrolyte material | Metal halide | Reaction temperature (° C.) | Electric conductivity (Scm$^{-1}$) |
|---|---|---|---|---|
| SE1 | 1 | silver iodide | 120 | $4.5 \times 10^{-4}$ |
| SE2 | 2 | silver iodide | 160 | $1.2 \times 10^{-3}$ |
| SE3 | 3 | silver iodide | 190 | $1.4 \times 10^{-2}$ |
| SE4 | 3 | copper iodide | 190 | $1.2 \times 10^{-2}$ |
| SE5 | 4 | silver iodide | 190 | $1.3 \times 10^{-2}$ |

TABLE 2-continued

| Solid Electrolyte | Solid electrolyte material | Metal halide | Reaction temperature (° C.) | Electric conductivity (Scm$^{-1}$) |
|---|---|---|---|---|
| SE6 | 4 | copper bromide | 190 | $1.1 \times 10^{-3}$ |
| SE7 | 5 | silver iodide | 170 | $8.8 \times 10^{-3}$ |
| SE8 | 5 | copper iodide | 170 | $1.0 \times 10^{-2}$ |
| SE9 | 6 | silver iodide | 190 | $1.6 \times 10^{-2}$ |
| SE10 | 7 | silver bromide | 160 | $6.5 \times 10^{-3}$ |
| SE11 | 7 | copper bromide | 170 | $9.0 \times 10^{-3}$ |

Table 2 shows that the solid electrolytes prepared according to the present invention can have an electric conductivity of at least $1 \times 10^{-4}$ Scm$^{-1}$. Further, it is seen that the solid electrolytes obtained by the use of cyclic amines have a higher electric conductivity.

The solid electrolytes obtained by the use of the polymers as a raw material showed lower hygroscopicity than those obtained by the use of the monomers. The solid electrolytes were evaluated for hygroscopicity on the basis of a weight increase when they were allowed to stand in a 25° C. and 80% RH atmosphere. Further, when the shaped products were compared on mechanical strength, the solid electrolyte pellets obtained by the use of the monomers were relatively fragile, while the pellets obtained by the use of the polymers, particularly SE3, SE4, SE5 and SE6, showed high mechanical strength. Of the solid electrolytes obtained by the use of polymers, SE3, SE4, SE5, SE6, SE10 and SE11, particularly SE5 and SE6, showed particularly desirable results, and these showed almost no hygroscopicity.

Preparation of Carbon Dioxide Sensor

While a silver/silver chloride electrode or a silver/silver oxide electrode was used for a reference electrode when the solid electrolyte was an Ag ion movement type or while a copper/copper oxide electrode was used when the solid electrolyte was a Cu ion movement type, sensors shown in Table 3 were prepared in the following procedures.

For the sensors in which the reference electrode of silver/silver chloride or silver/silver oxide was formed concurrently with the solid electrolyte and a detection electrode, first, 100 mg of a mixture containing a silver powder and a silver chloride power or a silver oxide powder for forming a reference electrode was placed in a mold and softly pressed. Then, 200 mg of a powder prepared by milling the heat-treated pellets obtained in the above synthesis step was charged thereon and softly pressed. Further, 50 mg of silver carbonate, etc., for forming a detection electrode was placed thereon and softly pressed. Then, the stacked materials were pressed at 700 kgf/cm$^2$ with reducing a pressure with a rotary pump, to give a laminate having a reference electrode, a solid electrolyte and a detection electrode. In this case, a platinum mesh was placed on the powder of the silver carbonate, etc., and after the above pressing was completed, a lead wire was connected to the platinum mesh.

When the reference electrode was a copper/copper oxide electrode, the reference electrode was formed in the same manner as above except that the silver powder was replaced with a copper powder and that the silver chloride powder or the silver oxide powder was replaced with a copper oxide powder.

In a sensor D, without forming the reference electrode concurrently, the solid electrolyte and the detection electrode were formed concurrently as described above, and then the reference electrode was formed on a surface opposed to the surface where the reference electrode was to be formed.

In this method, first, a paste of silver chloride was mixed with a commercially available epoxy electrically conductive silver paste to prepare a paste. The paste was applied to the silver mesh to which the lead wire had been connected, then, and the silver mesh was tightly attached to the above surface of the solid electrolyte, heat-treated at 90 to 150° C. to harden the paste and used a reference electrode.

Then, for preventing the contact of the solid electrolyte and the reference electrode to an atmosphere to be measured, the laminate formed of the reference electrode, the solid electrolyte and the detection electrode was embedded in a container so as to expose the detection electrode surface alone, whereby sensors having the structure shown in FIG. 1 were obtained. A container formed of hard vinyl chloride having almost no gas permeability and having a thickness of 1 mm was used as the container.

Table 3 shows a combination of the solid electrolyte, the detection electrode and the reference electrode in each sensor.

TABLE 3

| Sensor | Reference electrode | Detection electrode | Solid Electrolyte |
|---|---|---|---|
| A | Silver/silver chloride | Silver carbonate | SE2 |
| B | Silver/silver chloride | Silver carbonate | SE3 |
| C | Silver/silver chloride | Silver carbonate | SE5 |
| D | Silver/silver chloride | Silver carbonate | SE7 |
| E | Silver/silver chloride | Silver carbonate | SE10 |
| F | Silver/silver oxide | Silver carbonate | SE3 |
| G | Silver/silver oxide | Silver carbonate | SE5 |
| H | Silver/silver oxide | Silver carbonate | SE10 |
| I | Copper/copper oxide | Basic copper carbonate | SE4 |
| J | Copper/copper oxide | Basic copper carbonate | SE8 |
| K | Silver/silver chloride | Sodium carbonate/barium carbonate | SE5 |
| L | Silver/silver chloride | Lithium carbonate/calcium carbonate | SE5 |
| M | Silver/silver oxide | Sodium carbonate/barium carbonate | SE5 |
| N | Silver/silver oxide | Lithium carbonate/calcium carbonate | SE5 |
| O | Copper/copper oxide | Sodium carbonate/barium carbonate | SE6 |
| P | Copper/copper oxide | Lithium carbonate/calcium carbonate | SE6 |
| Q | Copper/copper oxide | Basic copper/carbonate | SE11 |
| R | Silver/silver oxide | Silver carbonate | SE1 |
| S | Silver/silver oxide | Silver carbonate | SE9 |

Examination of Sensor Characteristics

The following measurements were carried out with the sensors shown in Table 3.

First, the sensor was placed in a measurement container provided with an inlet and an outlet of gas, and air in the container was once softly pressure-reduced. Then, a gas mixture containing 80% nitrogen and 20% oxygen was charged. The cycle of the above pressure reduction and charging was repeated three times, to nearly completely discharge air in the container. Then, after the electromotive force of the sensor was found to be stabilized, the gas in the container was replaced with a test gas prepared by adding 1,000 ppm of carbon dioxide to the same gas mixture as above, and an electromotive force was measured then. The measurement of the electromotive force used a potentiostat having a large internal impedance. Then, the gas in the container was replaced with a test gas prepared by adding 100 ppm of carbon dioxide to the same gas mixture as above, and an electromotive force was measured in the same manner as above then. Finally, the gas in the container was again replaced with the same gas mixture as above, and an electromotive force was measured and compared with the electromotive force in the beginning. The carbon dioxide concentration was measured by gas chromatography, and all of the above measurements were carried out at room temperature.

As the result of the above measurements, it was found that that the electromotive forces of all the sensors shown in Table 3 changed nearly in proportion to the logarithm of carbon dioxide concentration and that when the carbon dioxide was removed after the measurements, the initial electromotive force was restored.

FIGS. 3, 4, 5 and 6 show graphs showing relationships between carbon dioxide concentration and electromotive force in the sensors D, E, I and Q, respectively. These Figures show that electromotive forces in proportion to logarithms of carbon dioxide concentrations were generated and that electromotive force changes sufficiently large for sensors were obtained. The sensors using neither silver carbonate nor copper carbonate in detection electrodes showed low response and showed small changes in electromotive force.

Each of the above sensors was excellent in responsiveness and exhibited a stabilized change in electromotive force after about 10 minutes.

When the test gas was modified to 50% RH, there was almost no influence on the stability of each of the above sensors, and the sensors using a polymer as a solid electrolyte material were less influenced.

When the solid electrolyte materials shown in the above Table 1 were replaced with solid electrolyte materials shown in the following Table 4, results similar to the above were obtained.

TABLE 4

| Solid electrolyte No. | State | Amine compound | Halogen compound |
|---|---|---|---|
| 8 | monomer | diethylmethylamine | ethyl iodide |
| 9 | monomer | N,N'-dimethylpiperazine | methyl iodide |
| 10 | monomer | 1-benzylpyridinium | ethyl iodide |
| 11 | monomer | N,N,N',N-tetramethyl-benzidine | methyl iodide |
| 12 | monomer | piperazine | ethyl iodide |
| 13 | monomer | N,N,N',N-tetramethyl-diaminoethane | methyl iodide |
| 14 | polymer | N,N'-dimethylpiperazine | 1,3-dibromo-propane |
| 15 | polymer | N,N'-dimethylpiperazine | 2-hydroxy-1,3-diiodobutane |
| 16 | polymer | N,N,N',N-tetramethyl-benzidine | 1,3-dibromo-propane |
| 17 | polymer | N,N,N',N-tetramethyl-diaminoethane | 1,3-dibromo-propane |
| 18 | polymer | N,N'-dimethylpiperazine | 1,4-diiodo-butane |
| 19 | polymer | N,N,N',N-tetramethyl-diaminoethane | 1,4-diiodo-butane |
| 20 | polymer | N,N,N',N-tetramethyl-benzidine | 1,4-diiodo-butane |

On the basis of the above results, it can be said that the sensor of the present invention can fully operate at room temperature.

Example 2
Preparation of Carbon Dioxide Sensor

The solid electrolyte material No. 4 synthesized in Example 1 (polymer from triethylenediamine and 1,3-dibromopropane) and silver iodide or copper iodide in a molar ratio of 1:7 were fully mixed in an agate mortar, and the mixture was pressed at 700 kgf/cm$^2$ to give a shaped material in the form of pellets. The shaped material was heat-treated under reduced pressure ($1\times10^{-3}$ Torr) at 190° C. for 16 hours, to give a solid electrolyte.

While a silver/silver chloride electrode or a silver/silver oxide electrode was used for a reference electrode when the solid electrolyte was an Ag ion movement type, or while a copper/copper oxide electrode was used when the solid electrolyte was a Cu ion movement type, sensors shown in Table 5 were prepared in the following procedures.

For the sensors in which the reference electrode of silver/silver chloride or silver/silver oxide was formed concurrently with the solid electrolyte and a detection electrode, first, 100 mg of a mixture containing a silver powder and a silver chloride power or a silver oxide powder for forming a reference electrode was placed in a mold and softly pressed. Then, 250 mg of a powder prepared by milling pellets of the above solid electrolyte was charged thereon and softly pressed. Further, 50 mg of a mixture powder of silver carbonate and lithium carbonate for forming a detection electrode was placed thereon and softly pressed. Then, the stacked materials were pressed at 700 kgf/cm$^2$ with reducing a pressure with a rotary pump, to give a laminate having a reference electrode, a solid electrolyte and a detection electrode. In this case, a platinum mesh was placed on the powder of the silver carbonate, etc., and after the above pressing was completed, a lead wire was connected to the platinum mesh.

When the reference electrode was a copper/copper oxide electrode, the reference electrode was formed in the same manner as above except that the silver powder was replaced with a copper powder and that the silver chloride powder or the silver oxide powder was replaced with a copper oxide powder. When the detection electrode was a lithium carbonate/copper carbonate electrode, the reference electrode was formed in the same manner as above except that the silver carbonate powder was replaced with a copper carbonate powder.

Then, for preventing the contact of the solid electrolyte and the reference electrode to an atmosphere to be measured, the laminate formed of the reference electrode, the solid electrolyte and the detection electrode was embedded in a container so as to expose the detection electrode surface alone, whereby sensors having the structure shown in FIG. 1 were obtained. A container formed of hard vinyl chloride having almost no gas permeability and having a thickness of 1 mm was used as the container.

Table 5 shows a combination of the metal carbonates of the detection electrode and the metal halide used for the solid electrolyte in each sensor.

TABLE 5

| Sensor | Detection electrode | Content of alkali metal carbonate (wt %) | Metal halide |
|---|---|---|---|
| a | Lithium carbonate/silver carbonate | 0 | Silver iodide |
| b | Lithium carbonate/silver carbonate | 1 | Silver iodide |

TABLE 5-continued

| Sensor | Detection electrode | Content of alkali metal carbonate (wt %) | Metal halide |
|---|---|---|---|
| c | Lithium carbonate/silver carbonate | 5 | Silver iodide |
| d | Lithium carbonate/silver carbonate | 10 | Silver iodide |
| e | Lithium carbonate/silver carbonate | 20 | Silver iodide |
| f | Lithium carbonate/silver carbonate | 30 | Silver iodide |
| g | Lithium carbonate/silver carbonate | 40 | Silver iodide |
| h | Lithium carbonate/silver carbonate | 50 | Silver iodide |
| i | Lithium carbonate/copper carbonate | 0 | Copper iodide |
| j | Lithium carbonate/copper carbonate | 20 | Copper iodide |

Examination of Sensor Characteristics

The following measurements were carried out with the sensors shown in Table 5.

First, the sensor was placed in a measurement container (to be referred to as "measurement cell" hereinafter) provided with an inlet and an outlet of gas, and air in the cell was once softly pressure-reduced. Then, pure Air (gas mixture containing 80% nitrogen and 20% oxygen) was charged, and then continuously flowed at a flow rate of 100 ml/minute. In this flow system, pure Air and pure Air A having an adjusted $CO_2$ concentration of 10,400 ppm are mixed with each other with a multi-flow meter 1203 (supplied by Kojima Seisakusho), and gas having any $CO_2$ concentration is flowed into the measurement cell. $CO_2$ concentrations were determined by sampling gas from the outlet of the cell and subjecting it to gas chromatography (column used: Porapack Q). The measurement cell has a volume of 60 cm$^3$ in a state where no element is fitted.

Then, after it was found that the electromotive force of the sensor was stabilized, an electromotive force was measured. The electromotive force measurement used a potentiostat HA-151 (internal impedance $10^{11}$ Ω, supplied by Hokuto Denko). In the consecutive measurements, the $CO_2$ concentration was changed, and after it was found that the electromotive force of the sensor was stabilized, an electromotive force was measured in the same manner. And, the sensor was evaluated for characteristics. The above measurements were all carried out at room temperature.

The results of the above measurements show that when the electromotive forces of all the sensors shown in Table 5 were plotted with regard to logarithms of the carbon dioxide concentrations, the relationships thereof were nearly like a straight line, i.e., linear. The inclinations of the straight lines were defined as changes in electromotive force.

Figure 7:
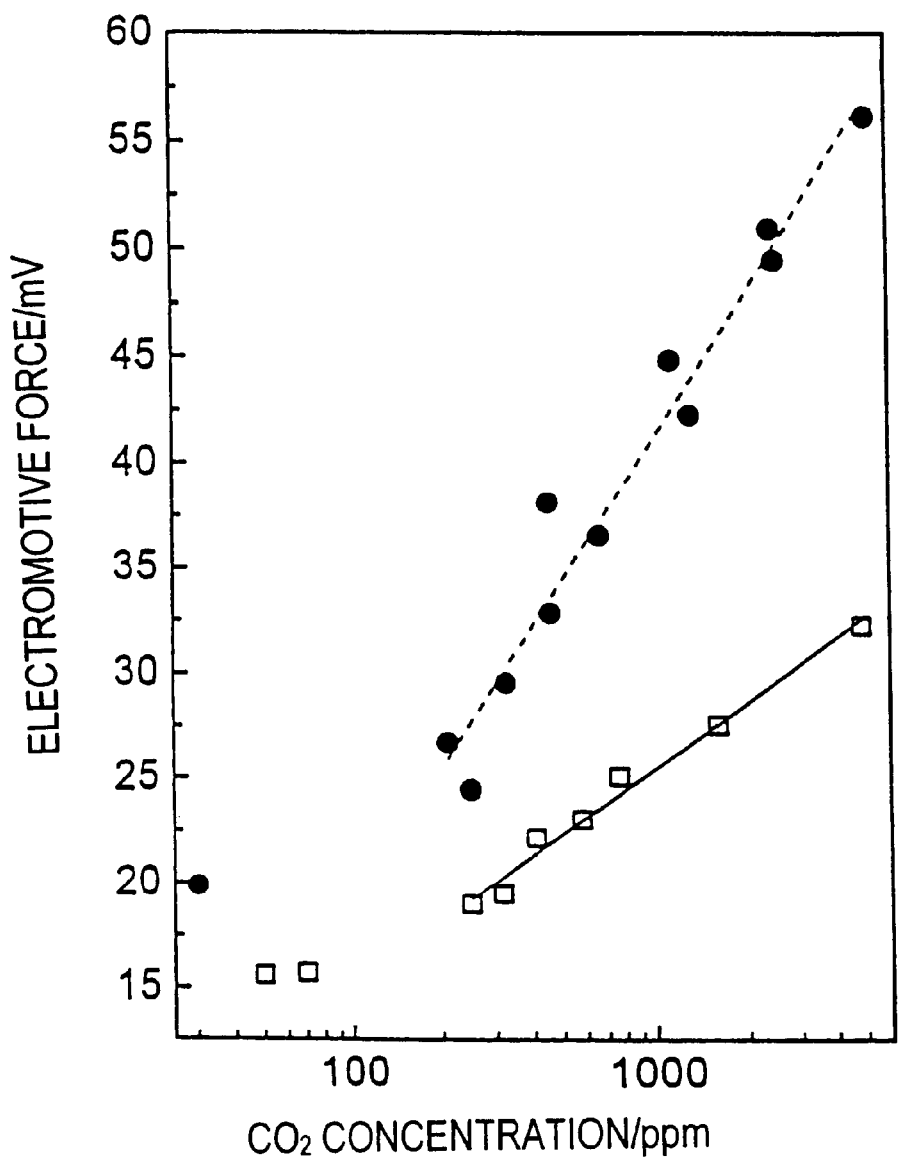
FIG. 7 is a graph showing a relationship between a carbon dioxide concentration and the electromotive force of a sensor a or c.

FIG. 7 shows a graph showing relationships between the carbon dioxide concentration and the electromotive force with regard to the sensor a and the sensor c. □ represents the sensor a and ● represents the sensor c. In these two, the relationship between the logarithms of carbon dioxide concentrations and the electromotive forces is liner, and it is shown that electromotive forces in proportion to the logarithms of the carbon dioxide concentrations were generated. Further, it is seen that the sensor c of which the detection electrode contains 5 wt % lithium carbonate shows a large change in electromotive force on the basis of a change in the carbon dioxide concentration as compared with the sensor a of which the detection electrode contains silver carbonate alone.

Figure 8:
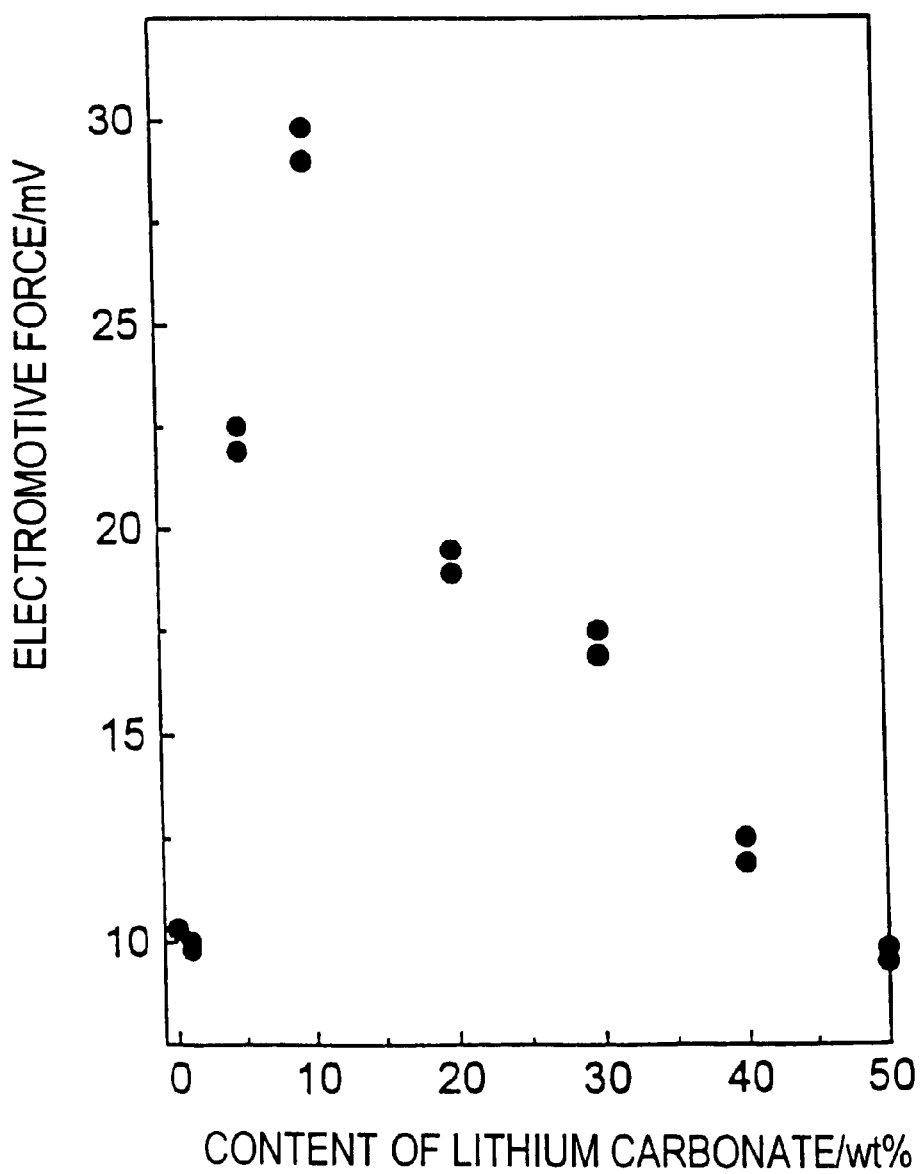
FIG. 8 is a graph showing a relationship between the amount of added lithium carbonate and a change in the electromotive force.

FIG. 8 shows relationships between the amount of added lithium carbonate and the change in electromotive force with regard to the sensors a to h. The electromotive force is maximal when the lithium carbonate content is 10 wt %, and the change in electromotive force increases. When the lithium carbonate content is in the range of from 5 to 40 wt %, the change in electromotive force is greater than that when no lithium carbonate is added. Further, when the lithium carbonate content is 50 wt %, the sensor shows a change in electromotive force which change is approximately equivalent to that when no lithium carbonate is contained.

The sensors i and j using copper carbonate as a main component were also studied with regard to the change in electromotive force. The change of the sensor i using no lithium carbonate in electromotive force was 8 mV/decade, and the change of the sensor j having a lithium carbonate content of 20 wt % in electromotive force was 22 mV/decade, which was 2.75 times as large as that of the sensor i. The sensor using copper carbonate as main component exhibited an effect similar to that of the sensor using silver carbonate as a main component.

In addition, the above sensors were also excellent in responsiveness and their change in electromotive force was stabilized after about 10 minutes.

Example 3

Sensors having a temperature detection element and a humidity detection element and having a structure shown in FIG. 2 were prepared using the carbon dioxide sensors a, d, e, i and j prepared in Examples 2. A temperature and humidity detection element CHS-TUGS11 in which the two elements were integrated (supplied by TDK Corporation) was used as the temperature detection element and the humidity detection element. The above element measures a temperature by a thermistor method and a humidity by an electric resistance method, and a value for each is obtained as a voltage output.

Table 6 shows a combination of metal carbonates of the detection electrode and a metal halide used in the solid electrolyte in each sensor. The sensors a1, d1, e1, i1 and j1 used the sensors a, d, e, i and j obtained in Example 2.

TABLE 6

| Sensor | Detection electrode | Content of alkali metal carbonate (wt %) | Metal halide |
|---|---|---|---|
| a1 | Lithium carbonate/silver carbonate | 0 | Silver iodide |
| d1 | Lithium carbonate/silver carbonate | 10 | Silver iodide |
| e1 | Lithium carbonate/silver carbonate | 20 | Silver iodide |
| i1 | Lithium carbonate/copper carbonate | 0 | Copper iodide |
| j | Lithium carbonate/copper carbonate | 20 | Copper iodide |

The following measurements were carried out with the sensors shown in Table 6. In measurements, carbon dioxide was measured for an electromotive force with a potentiostat HA-151 (internal impedance $10^{11}$ Ω, supplied by Hokuto Denko), and at the same time, a resistance value of the temperature detection element and an electromotive force of the humidity detection element were measured with a digital multi-meter $TR_{6846}$ (supplied by Advantest).

First, the sensor was placed in a measurement container (to be referred to as "measurement cell", hereinafter) provided with an inlet and an outlet of gas, and air in the cell was- once softly pressure-reduced. Then, pure Air (gas mixture containing 80% nitrogen and 20% oxygen) was charged, and then continuously flowed at a flow rate of 100 ml/minute. In this flow system, pure Air and pure Air A having an adjusted $CO_2$ concentration of 10,400 ppm are mixed with each other with a multi-flow meter 1203 (supplied by Kojima Seisakusho), and gas having any $CO_2$ concentration is flowed into the measurement cell. $CO_2$ concentrations were determined by sampling gas from the outlet of the cell and subjecting it to gas chromatography (column used: Porapack Q). The measurement cell has a volume of 60 cm$^3$ in a state where no element is fitted. Then, after it was found that the electromotive force of the carbon dioxide sensor element was stabilized, an electromotive force, a temperature and a humidity were measured at a point of that time.

First, the temperature characteristic and the humidity characteristic of the electromotive force of the carbon dioxide sensor element were measured.

The temperature characteristic was measured by changing temperatures while the measurement cell was in a constant-temperature chamber in an atmosphere having a humidity fixed to 0% and a $CO_2$ concentration fixed to 300 ppm.

Figure 9:
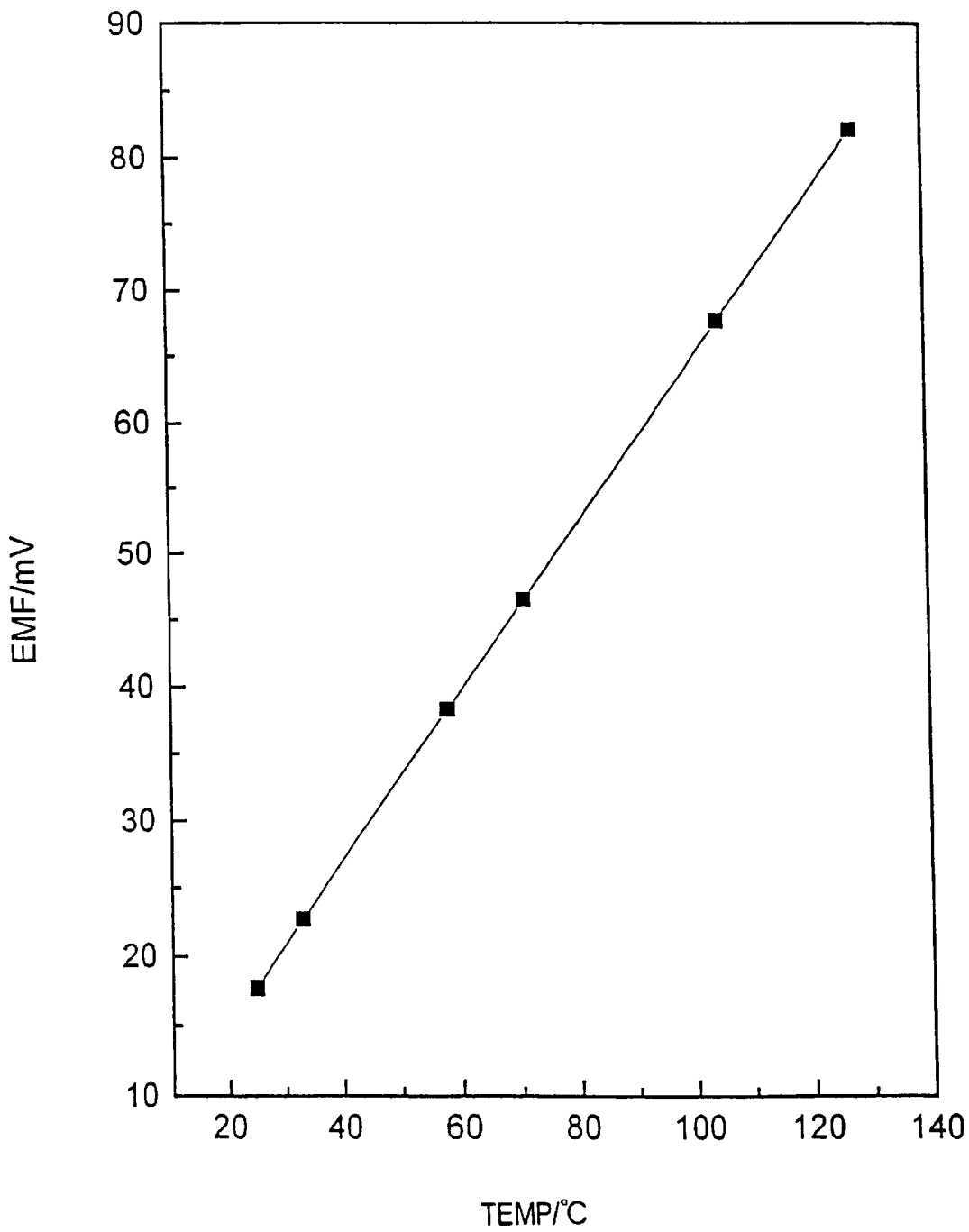
FIG. 9 is a graph showing a relationship between the electromotive force of a carbon dioxide sensor element of a sensor dl and a temperature.

FIG. 9 shows the temperature characteristic of the sensor d1. The electromotive force of the carbon dioxide sensor element nearly had a linear relationship with the temperature, and the relational expression thereof was $$E=0.625 \text{ mV/k} \times T+2.0 \text{ mV}$$

in which E is an electromotive force of the carbon dioxide sensor element and T is a temperature measured with the temperature detection element.

The humidity characteristic was measured by generating an atmosphere having a temperature fixed to 25° C. and a $CO_2$ concentration fixed to 300 ppm in a precision humidity generating apparatus (Shin-ei sr-1) and changing a relative humidity from 0% to 100% consecutively at a change rate of 10%.

Figure 10:
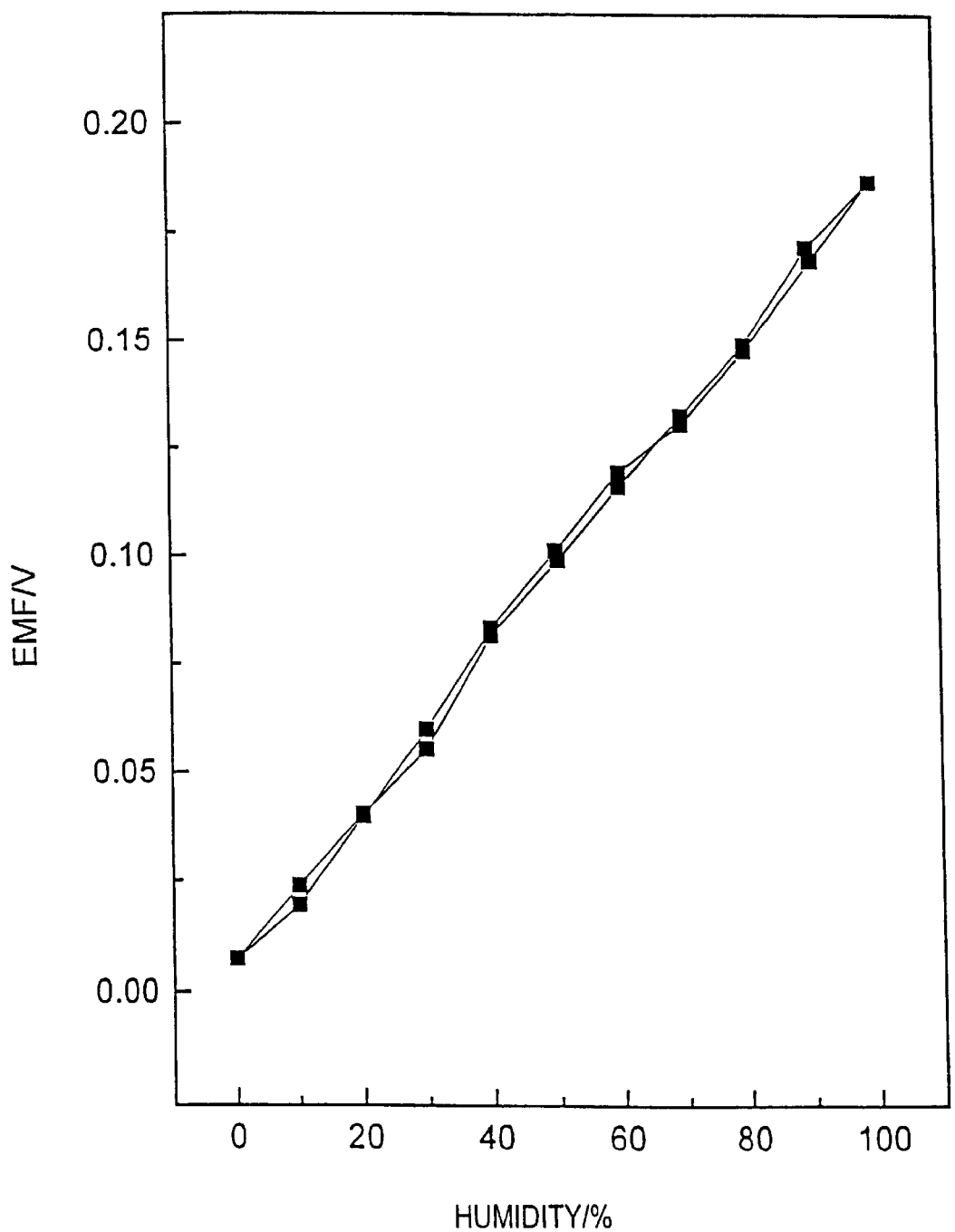
FIG. 10 is a graph showing a relationship between the electromotive force of a carbon dioxide sensor element of a sensor d1 and a humidity.

FIG. 10 shows the humidity characteristic of the sensor 1d. The electromotive force of the carbon dioxide sensor element nearly had a linear relationship with the humidity, and the relational expression thereof was $$E=1.81 \text{ mV} \times H+5.9 \text{ mV}$$

in which E is an electromotive force of the carbon dioxide sensor element and H is a humidity measured with the humidity detection element.

Then, the $CO_2$ concentration was consecutively varied, and after it was found that the electromotive force of the carbon dioxide sensor element was stabilized, electromotive forces were measured to evaluate the sensor characteristic.

As a result of the above measurement, it was found that when the electromotive forces of all the sensors shown in Table 6 were plotted with regard to logarithms of the carbon dioxide concentrations, the relationships thereof were nearly like straight lines, i.e., linear.

Figure 11:
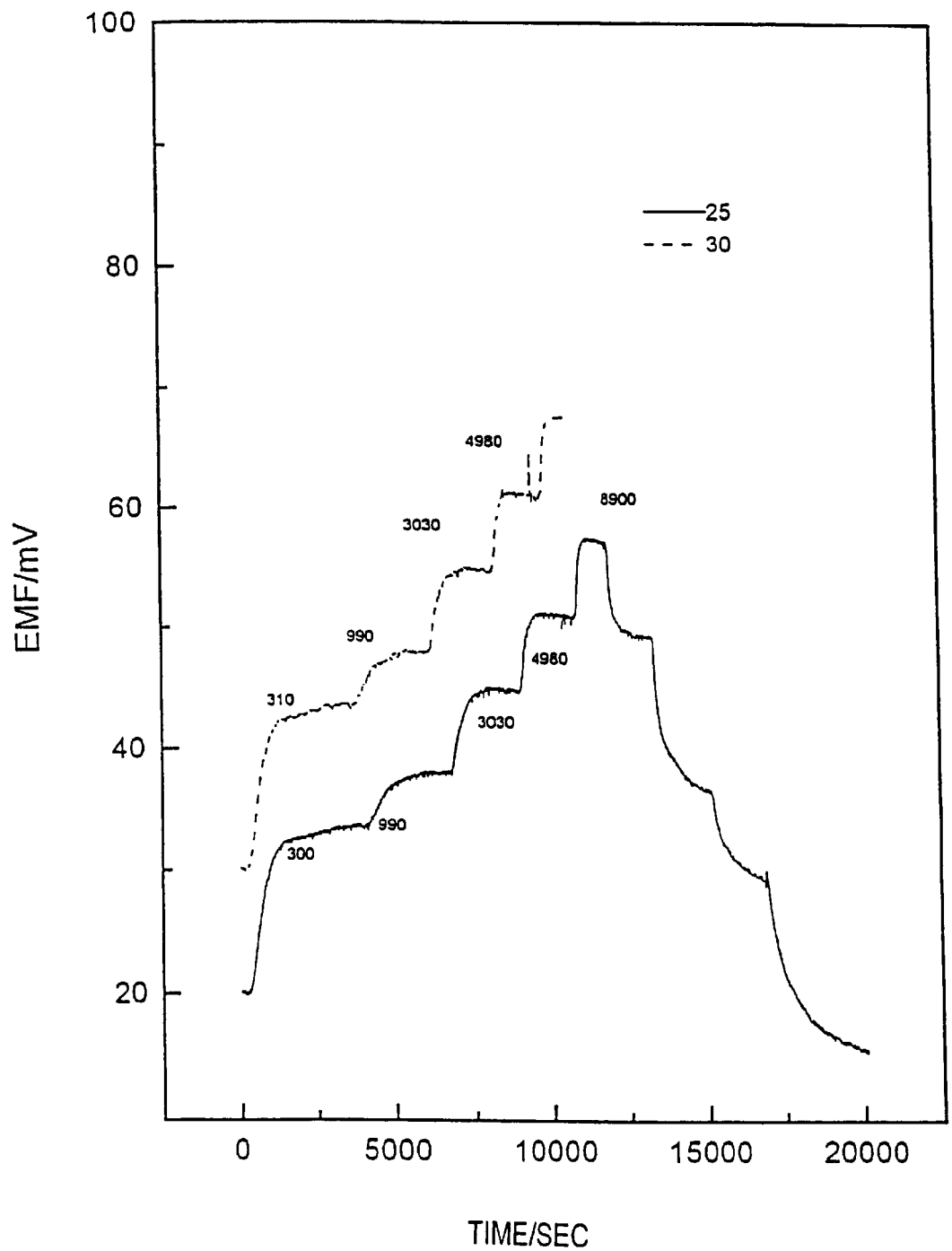
FIG. 11 is a graph showing a change of electromotive force of a carbon dioxide sensor element of a sensor dl before correction, with the passage of time.

FIG. 11 shows a change of the electromotive force (measured with the carbon dioxide sensor element) before correction at a measurement temperature changed to 25° C. and 30° C. with the passage of time with regard to the sensor d1. Figures in the graph are carbon dioxide concentrations. The above measurements were carried out at a humidity of 0%.

Figure 12:
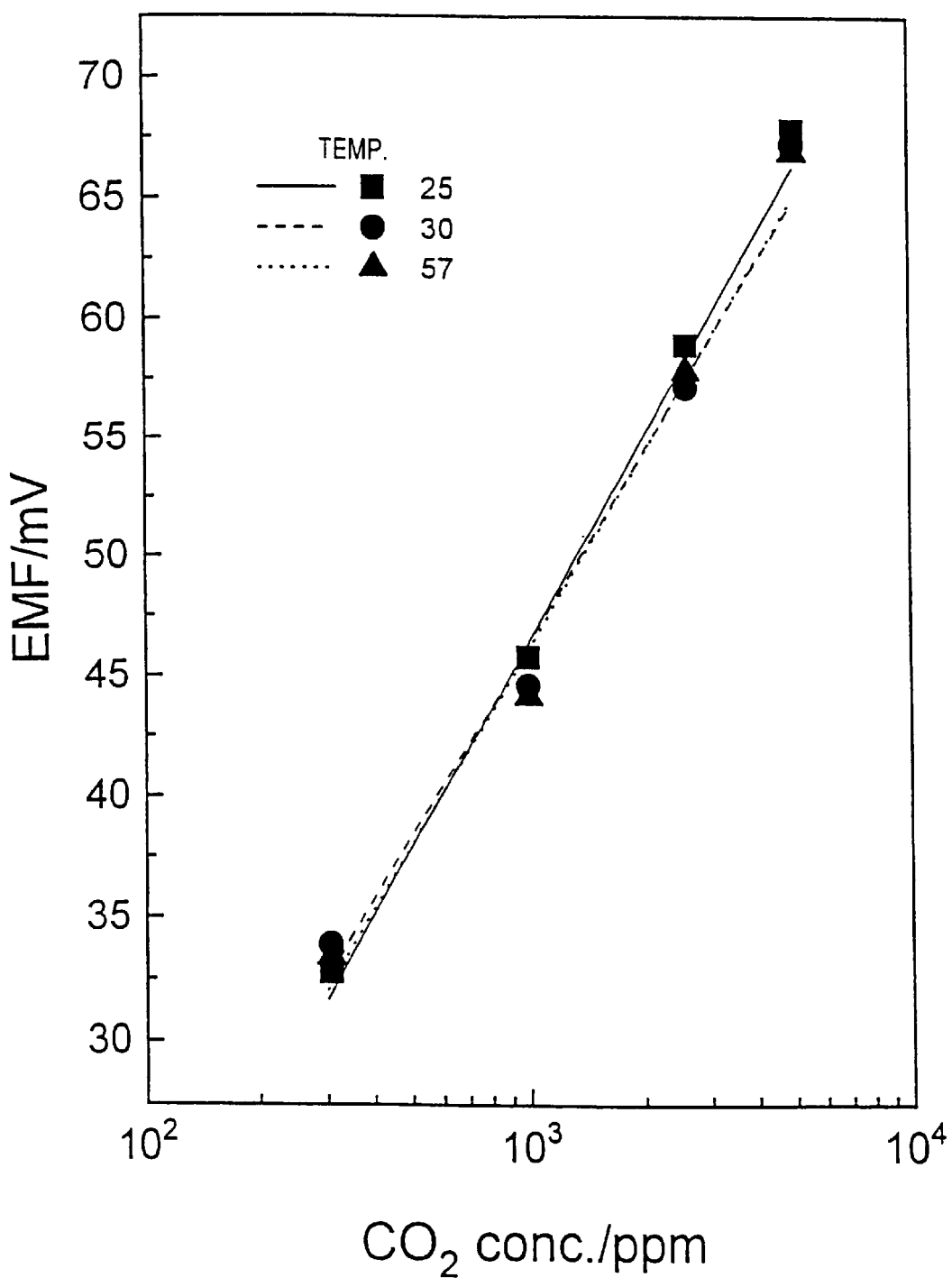
FIG. 12 is a graph showing a relationship between the electromotive force of a sensor dl after correction with regard to a temperature and a carbon dioxide concentration.

FIG. 12 shows data obtained by correcting measurement data in FIG. 11 to values at 25° C. on the basis of the relational expression between the electromotive force and the temperature determined in FIG. 9 and plotting the values with regard to logarithms of the carbon dioxide concentrations. Further, FIG. 12 also shows the results of measurement at 57° C. The correction with regard to the temperature was conducted on the basis of the following expression.

$$E'=E-0.625 \text{ mV/k} \times (T-25)$$

in which E' is a corrected electromotive force, E is an electromotive force found and T is a measurement temperature. The carbon dioxide concentration was determined by substituting the corrected electromotive force in the following expression.

$$E'=28.1 \times \log C-37.6$$

in which E' is a corrected electromotive force and C is a carbon dioxide concentration. Electromotive forces measured at any temperature were corrected to nearly the same value, and it is seen that the influence caused by a change in temperature can be corrected by the above method.

Figure 13:
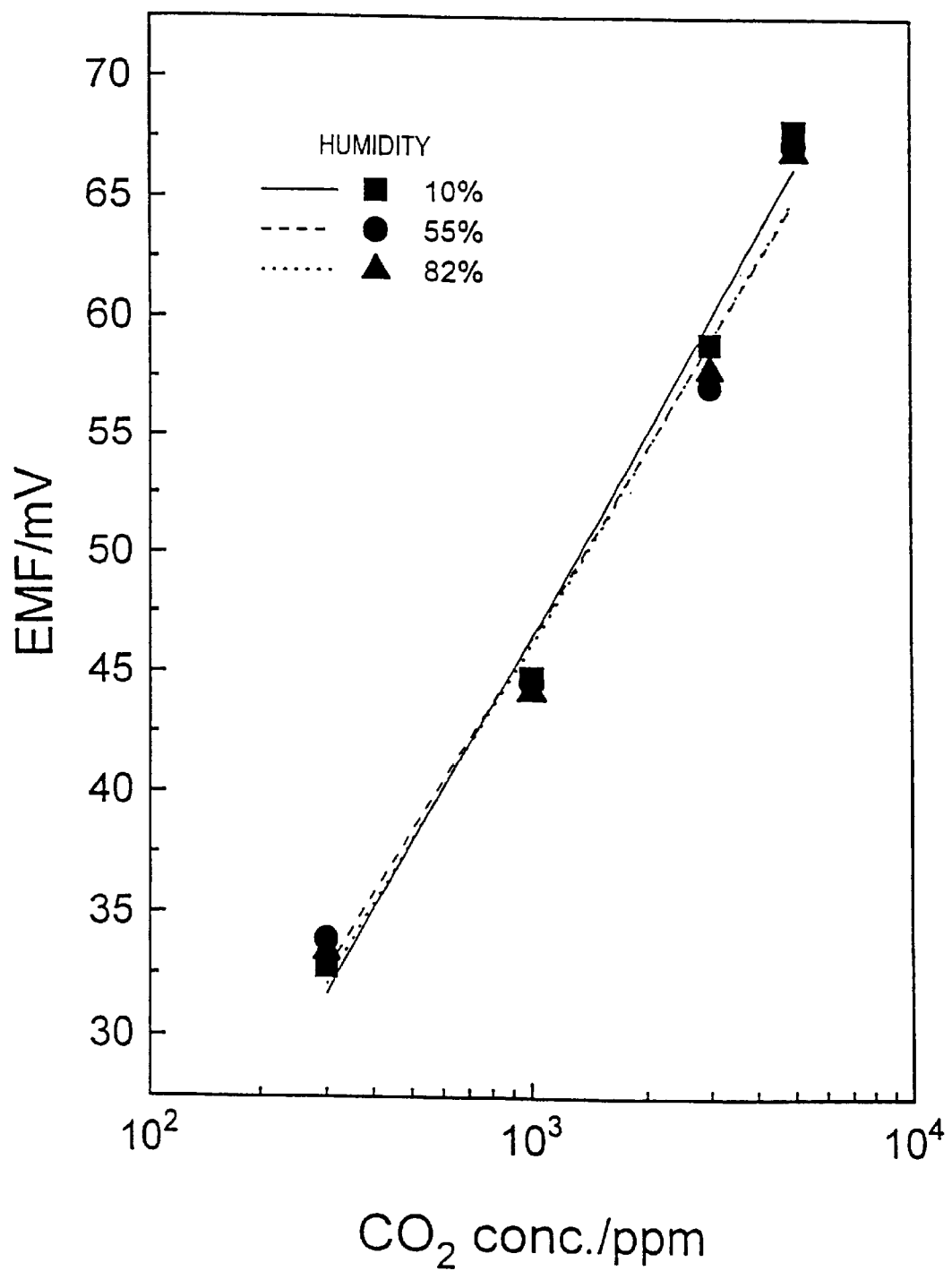
FIG. 13 is a graph showing a relationship between the electromotive force of a sensor dl after correction with regard to a humidity and a carbon dioxide concentration.

FIG. 13 shows data obtained by measuring the sensor for electromotive forces at an ambient measurement humidity changed to 10%, 55% and 82%, correcting the measurement values to values at 10% on the basis of the relational expression between the electromotive force and the temperature determined in FIG. 10 and plotting the values with regard to logarithms of carbon dioxide concentrations. The above measurements were carried out at 25° C. The correction with regard to humidity was conducted on the basis of the following expression.

$$E'=E-1.81 \text{ mV} \times (H-10)$$

in which E' is a corrected electromotive force, E is an electromotive force found and H is a measurement humidity. The carbon dioxide concentration was determined on the basis of the corrected electromotive force in the same manner as in the correction with regard to the temperature. Electromotive forces measured at any humidity were corrected to nearly the same value, and it is seen that the influence caused by a change in humidity can be corrected by the above method.

Results similar to those of the sensor d1 were obtained with regard to the other sensors, and changes in outputs of the carbon dioxide sensor elements with regard to the temperature and humidity were corrected by the above methods.

EFFECT OF THE INVENTION

As explained above, according to the present invention, there can be obtained a solid electrolyte which operates at room temperature and has high stability against humidity. Further, there can be provided a carbon dioxide sensor having not only sufficient sensitivity but also excellent responsiveness at room temperature and having excellent humidity resistance, and further, a carbon dioxide sensor which exhibits, besides these, a large change on the basis of a change in carbon dioxide concentration. According to the present invention, further, there can be provided a highly accurate carbon dioxide sensor which has sufficiently high sensitivity at room temperature and is also free from influences caused by humidity and temperature and an output correction thereof.

What is claimed is:

1. A solid electrolyte formed by heat-treating a polymer having a quaternary ammonium group in its main chain and having a halide ion as counter ion, and a metal halide at at least 100° C.

2. The solid electrolyte according to claim 1, wherein the polymer is a polymer from a diamine compound and a dihalogen compound.

3. The solid electrolyte according to claim 1, wherein the metal halide is a halide of Ag or Cu.

4. A carbon dioxide sensor, comprising a detection electrode and a reference electrode formed respectively in contact with a solid electrolyte, the detection electrode containing a metal carbonate which forms a dissociation equilibrium with carbon dioxide, wherein the solid electrolyte is a product formed by heat-treating a polymer having a quaternary ammonium group in its main chain and having a halide ion as counter ion, and a metal halide at at least 100° C.

5. The carbon dioxide sensor according to claim 4, wherein the polymer is a polymer from a diamine compound and a dihalogen compound.

6. The carbon dioxide sensor according to claim 4, wherein the metal halide is a halide of Ag or Cu.

7. The carbon dioxide sensor according to claim 4, wherein the detection electrode contains at least 2 metal carbonates which form dissociation equilibrium with carbon dioxide.

8. The carbon dioxide sensor according to claim 7, wherein the metal carbonates are silver carbonate and an alkali metal carbonate.

9. The carbon dioxide sensor according to claim 8, wherein the alkali metal carbonate is contained in an amount of 50% by weight or less.

10. The carbon dioxide sensor according to claim 9, wherein the alkali metal carbonate is contained in an amount of 5 to 10% by weight.

11. The carbon dioxide sensor according to claim 7, wherein the metal carbonates are copper carbonate and an alkali metal carbonate.

12. A carbon dioxide sensor device having the carbon dioxide sensor recited in claim 4 and further having a temperature detection element for detecting a temperature of the carbon dioxide sensor and/or a humidity detection element for detecting a humidity around the carbon dioxide sensor.

13. An output correction method which comprises providing the carbon dioxide sensor device recited in claim 4 measuring an electromotive force with the carbon dioxide sensor and at the same time, detecting a temperature with a temperature detection element, correcting the electromotive force with a linear relational expression of the electromotive force and the temperature, and determining a carbon dioxide concentration on the basis of the corrected electromotive force.

14. An output correction method which comprises providing the carbon dioxide sensor device recited in claim 4, measuring an electromotive force with the carbon dioxide sensor and at the same time detecting a humidity with a humidity detection element, correcting the electromotive force with a linear relational expression of the electromotive force and the humidity, and determining a carbon dioxide concentration on the basis of the corrected electromotive force.

15. An output correction method which comprises providing the carbon dioxide sensor device recited in claim 4, measuring an electromotive force with the carbon dioxide sensor and at the same time detecting a temperature with a temperature detection element and detecting a humidity with a humidity detection element, correcting the electromotive force with a linear relational expression of the electromotive force and the temperature and a linear relational expression of the electromotive force and the humidity, and determining a carbon dioxide concentration on the basis of the corrected electromotive force.

16. A method for preparing a solid electrolyte, comprising:

heat-treating a polymer and a metal halide at at least 100° C., wherein said polymer comprises a quaternary ammonium group in its main chain and a halide ion counter ion.

* * * * *

UNITED STATES PATENT AND TRADEMARK OFFICE
CERTIFICATE OF CORRECTION

PATENT NO.   : 6,241,873 B1                                    Page 1 of 1
DATED        : June 5, 2001
INVENTOR(S)  : Kenryo Namba et al.

It is certified that error appears in the above-identified patent and that said Letters Patent is hereby corrected as shown below:

Title page,
Item [54], title of the invention, "SOLD ELECTROLYTES, CARBON DIOXIDE SENSORS AND METHOD FOR CORRECTING THE OUTPUT OF SENSORS", should read -- SOLID ELECTROLYTES, CARBON DIOXIDE SENSORS AND METHOD FOR CORRECTING THE OUTPUT OF SENSORS --.

Item [30], Foreign Application Priority Data,
"Foreign Application Priority Data
Feb. 20, 1997   (JP) ..................................10-055935
Feb. 18, 1998   (JP) ..................................10-052966",
should read
-- Foreign Application Priority Data
Feb. 20, 1998   (JP) ..................................10-055935
Feb. 18, 1998   (JP) ..................................10-052966 --.

Signed and Sealed this

Eighteenth Day of December, 2001

*Attest:*

JAMES E. ROGAN
*Attesting Officer*       *Director of the United States Patent and Trademark Office*